(12) United States Patent
Thorpe et al.

(10) Patent No.: US 10,691,774 B2
(45) Date of Patent: Jun. 23, 2020

(54) SYSTEMS AND METHODS FOR A COMPREHENSIVE ONLINE HEALTH CARE PLATFORM

(71) Applicant: Cambia Health Solutions, Inc., Portland, OR (US)

(72) Inventors: Alexander Thorpe, Beaverton, OR (US); Nicole Cathcart, Portland, OR (US); Sean Karbowicz, Portland, OR (US)

(73) Assignee: CAMBIA HEALTH SOLUTIONS, INC., Portland, OR (US)

( * ) Notice: Subject to any disclaimer, the term of this patent is extended or adjusted under 35 U.S.C. 154(b) by 292 days.

(21) Appl. No.: 15/085,746

(22) Filed: Mar. 30, 2016

(65) Prior Publication Data

US 2016/0292367 A1    Oct. 6, 2016

Related U.S. Application Data

(60) Provisional application No. 62/140,374, filed on Mar. 30, 2015.

(51) Int. Cl.
| | | |
|---|---|---|
| *G16H 70/00* | (2018.01) | |
| *G06F 19/00* | (2018.01) | |
| *G16H 20/90* | (2018.01) | |
| *G16H 20/10* | (2018.01) | |
| *G16H 20/60* | (2018.01) | |
| *G16H 20/70* | (2018.01) | |
| *G16H 70/60* | (2018.01) | |
| *G16H 70/40* | (2018.01) | |

(52) U.S. Cl.
CPC ........ *G06F 19/326* (2013.01); *G06F 19/3456* (2013.01); *G16H 20/10* (2018.01); *G16H 20/60* (2018.01); *G16H 20/70* (2018.01); *G16H 20/90* (2018.01); *G16H 70/40* (2018.01); *G16H 70/60* (2018.01)

(58) Field of Classification Search
CPC ... G06F 19/326; G06F 19/3456; G16H 70/40; G16H 70/60; G16H 20/10; G16H 20/60; G16H 20/70; G16H 20/90
USPC .......................................................... 705/2
See application file for complete search history.

(56) References Cited

U.S. PATENT DOCUMENTS 6,000,828 A    12/1999  Leet
6,081,786 A     6/2000  Barry et al.
(Continued)

*Primary Examiner* — Robert A Sorey
*Assistant Examiner* — Kimberly A. Sass
(74) *Attorney, Agent, or Firm* — McCoy Russell LLP

(57) ABSTRACT

Systems and methods for a comprehensive online healthcare platform are provided that increase the efficiency of the medication selection process. In one embodiment, a method comprises responsive to a query from the user via the user device, receiving a list of one or more medications identified from a storage device and receiving medication information about each identified medication in the list of the one or more medications from the storage device. The method further includes, calculating a user personalized grade for each of the identified medications based on the medication information and the user information, transmitting the user personalized grade and medication information to the user device and displaying simultaneously on the user device, the user personalized grade, cost factor, prescription experience data, and secondary technical effects of each identified medication.

20 Claims, 17 Drawing Sheets

(56) References Cited

U.S. PATENT DOCUMENTS

| | | |
|---|---|---|
| 8,160,901 B2 | 4/2012 | Heywood et al. |
| 8,548,937 B2 | 10/2013 | Saigal et al. |
| 8,655,682 B2 | 2/2014 | Srivastava et al. |
| 8,655,817 B2 | 2/2014 | Hasey et al. |
| 8,712,797 B1 | 4/2014 | Bezdek et al. |
| 8,744,867 B2 | 6/2014 | Spertus |
| 8,793,245 B2 | 7/2014 | Kwete |
| 2003/0163353 A1 | 8/2003 | Luce et al. |
| 2008/0015894 A1* | 1/2008 | Miller ............... G06F 19/3456 705/2 |
| 2008/0097792 A1 | 4/2008 | Marge |
| 2009/0076857 A1 | 3/2009 | Eletreby et al. |
| 2011/0270843 A1* | 11/2011 | Albin .................... G06F 16/951 707/741 |
| 2012/0150562 A1* | 6/2012 | Lerner .................. G06Q 50/22 705/3 |
| 2012/0197655 A1 | 8/2012 | Debgupta et al. |
| 2012/0232936 A1 | 9/2012 | Bravata et al. |
| 2012/0259654 A1 | 10/2012 | Vanderzee et al. |
| 2012/0259662 A1 | 10/2012 | Vanderzee et al. |
| 2013/0238353 A1* | 9/2013 | Hennenfent .......... G06F 19/328 705/2 |
| 2014/0214441 A1* | 7/2014 | Young .................... G16H 10/20 705/2 |
| 2014/0244292 A1* | 8/2014 | Rosenberg ............ G06F 19/324 705/2 |
| 2014/0379610 A1* | 12/2014 | Lindeman .......... G06Q 30/0282 705/347 |

* cited by examiner

FIG. 8D

How Well is Testosterone Therapy Working for You?

If you've recently started testosterone therapy, it's important to keep talking to your doctor about your experience. There is little evidence that testosterone therapy for "low T" will improve your health. Additionally, the FDA released new evidence about serious safety risks.

Has your doctor helped you understand your risks?

The FDA and professional practice groups, like the Endocrine Society and the American Urological Association, are increasingly concerned about the long-term safety of testosterone therapy in aging men.

Recent studies have identified that testosterone replacement use may increase the risk of heart attacks and strokes in middle-age and older men.

How do you know if the therapy is working?

- Have you or your partner noticed a significant improvement in libido or sexual pleasure?
- Do you have energy now for things you couldn't do before?
- Have your family, friends or co-workers noticed an improvement in your mood?

If you answered NO to these questions, talk to your doctor about whether Testosterone therapy is right for you.

| Evidence A | Exercise/Weight Loss |
|---|---|

Multiple large studies have shown that diet, vigorous exercise and weight loss:
- Increase testosterone levels
- Improve symptoms of low T such as low energy and libido
- Increase heart health

Safety notes: Proper exercise generally carries a low risk of adverse effects

Price comparison: Variable, starting at no cost

| Evidence D | Testosterone Therapy |
|---|---|

Testosterone replacement products have only been shown to increase testosterone levels.
- It is unknown if testosterone replacement therapy improves quality of life or physical functioning.
- Although some people may experience a small benefit, there is no high-quality evidence that testosterone significantly improves low mood, sexual function, athletic performance, or energy levels.

The FDA has identified a possible increased risk of adverse cardiovascular outcomes (increased mortality, heart attack, and stroke).

Price comparison: AndroGel: $512 , Axiron: $461 Generic injectable: $54

What should I do?

Talk to your doctor

If you're currently using testosterone, you can discuss the potential risks and evaluate your benefits.

Do NOT make changes or stop using any medication without talking to your doctor or pharmacist first.

Get more information now

Visit www.OmedaRxEvidence.com/Testosterone to learn more about your options and review the evidence.

*A = high quality evidence, D = insufficient evidence of benefit
© OmedaRx 2015*

FIG. 8G

SYSTEMS AND METHODS FOR A COMPREHENSIVE ONLINE HEALTH CARE PLATFORM

CROSS REFERENCE TO RELATED APPLICATIONS

The present application claims priority to U.S. Provisional Patent Application No. 62/140,374, entitled "SYSTEMS AND METHODS FOR A COMPREHENSIVE ONLINE HEALTH CARE PLATFORM," and filed on Mar. 30, 2015, the entire contents of which are hereby incorporated by reference for all purposes.

BACKGROUND/SUMMARY

In the modern world, consumers are accustomed to a wide array of options when shopping for goods and services. Furthermore, online shopping at marketplaces such as Amazon, enable consumers to make informed purchasing decisions by comparing products by their price, quality, user reviews, user comments, etc. However, in today's health care marketplace, consumers are unable to compare medications using the same consumer tools as available in other marketplaces. Many health conditions have a variety of potential medications used for treatment. For example, there are a plurality of types of prescription medications used to treat high blood pressure. However, sorting through, comparing, and selecting a medication may be a time consuming, and even ineffective process. Patients may end up spending more money on a medication that is less effective than other lower-priced counterparts. Given the limited time patients have with doctors and the limited knowledge patients have about the differences between medications, the large number of potential medications often present an obstacle to productive patient involvement in the process of selecting a medication.

Patients and doctors face several obstacles in determining the most effective, safe and least costly medication option. First, because of the lack of transparency in the medication selection process, there are a substantial number of medication alternatives that may be overlooked by both patients and doctors. Many factors may be considered by a patient when selecting a medication: the effectiveness, cost, side effects, health risks, etc., of the medication. However, currently, patients are not able to compare all medication options produced by different companies, side by side by their relevant information. Currently, patients may sort through medications by price, or effectiveness, or by side effects. However, it may be more efficient for a patient to be able to compare the relevant information for all medications on one display. In doing so, patients can more easily find the most effective, safe, and least costly medication option. Further, enabling patients to sort medications based on their preferences may increase the transparency of medication options. As an example, if the cost of a medication is a priority for the patient, the patient could sort the medication from lowest to highest cost while still being able to view and compare other aspects of the medications such as their effectiveness, side effects, etc.

Second, patients with the same condition who use the same medication will often experience different outcomes. Said another way, the effectiveness of a medication may not be the same for all patients. Differences in a patient's medical information, such as their medical history, age, gender, currently prescribed medications, etc., may all affect the effectiveness of a medication in treating a patient's medical condition. Non-medical information such as a patient's lifestyle, values, preferences, work condition, financial condition, etc., may also affect the effectiveness of a medication. As such, the predicted effectiveness of a medication should reflect a patient's medical and non-medical information. Current attempts to predict the effectiveness of a medication may be based on clinical studies, and published scientific literature concerning the medication. However, these attempts may assign a fixed user personalized grade to the medication, without accounting for patient-to-patient differences.

Third, in the United States, the time doctors spend with patients to understand their individual situations is getting shorter and shorter, as both caseloads and administrative loads increase faster than the physician population. As a result, doctors may avoid shared decision making and patient-centered care because it takes more time to understand what is personal about a patient's feelings and situation and how to apply that to a medication choice. This is a problem because studies show that patients who are more involved in choosing their care tend to get better outcomes. Accordingly, there is a need in the art for improved methods and systems for helping patients select medications.

Several attempts to address transparency issues in the process of selecting medication have been made. For example, US patent application 2014/0,244,292 discloses a method for recommending treatment options to patients based on the predicted effectiveness of the treatment option. The predicted effectiveness may take into account medical and non-medical characteristics of the patient to improve the accuracy of the predicted effectiveness. Thus, the predicted effectiveness of a medication may depend on the patient, and as such a medication's predicted effectiveness may be personalized to each patient according to their specific traits and characteristics.

However, the inventors herein have recognized issues with the previous attempts to address the lack of transparency in the process of selecting medications. Specifically, previous attempts to increase the transparency of medication options only partially solve the issues described above. For example, US patent application 2014/0,244,292 only allows a patient to compare treatment options by their predicted effectiveness. Thus, only being able to compare treatment options by their effectiveness, may lead to a confusing and time consuming treatment selection process.

The inventors herein have recognized the issues described above and have devised systems and methods for addressing the issues. In particular, systems and methods for a transparent healthcare platform and user interface are provided. More specifically, the methods and systems described herein, provide an approach for integrating crucial and relevant information about medication options such as their effectiveness, cost, user reviews and comments, etc., and then compiles that information for a list of medications into one integrative display.

The present invention provides, among other advantages, methods and systems for helping patients find, select, compare, and purchase medications. In one embodiment, a method comprises receiving user information including one or more characteristics of a user from a remote user device, responsive to a query from the user via the user device, receiving a list of one or more medications identified from a storage device, receiving medication information about each identified medication in the list of the one or more medications from the storage device, wherein the received medication information includes one or more of an indication of the clinical effectiveness of the identified medications, prescription experience data characterizing experiences of patients with the identified medications, cost information, insurance coverage, care provider recommendations, and secondary technical effects, calculating a user personalized grade for each of the identified medications based on the medication information and the user information, transmitting the user personalized grade and medication information to the user device, and displaying simultaneously on the user device, the user personalized grade, cost, prescription experience data, and secondary technical effects of each identified medication.

In this way, a healthcare platform is provided that allows patients to search for, compare, select, and purchase medication all from one device. Thus, the efficiency of the process of selecting and purchasing a medication may be improved in two ways. First, because of the increased transparency of the medication options available to the patient, a patient may spend less money and experience improved results from their medications. Second the amount of time a patient may spend selecting a medication may be decreased due to the research, selection, and purchasing processes all being combined into one integrative process. Further, the safety of a patient may be improved due to the healthcare platform providing a patient-care provider integrated network. The patient profile including all of the patient's current medication may be monitored by the patient's care provider to ensure that any health risks associated with one or more of the medication may be avoided.

The above summary is provided to introduce a selection of concepts in a simplified form that are further described below in the Detailed Description. This summary is not intended to identify key features or essential features of the subject matter, nor is it intended to be used to limit the scope of the subject matter. Furthermore, the subject matter is not limited to implementations that solve any or all of the disadvantages noted above or in any part of this disclosure.

BRIEF DESCRIPTION OF THE FIGURES

FIG. 8D illustrates an example online health care platform interface for a user.

FIG. 8G illustrates an example online health care platform interface for a user.

DETAILED DESCRIPTION

Figure 1:
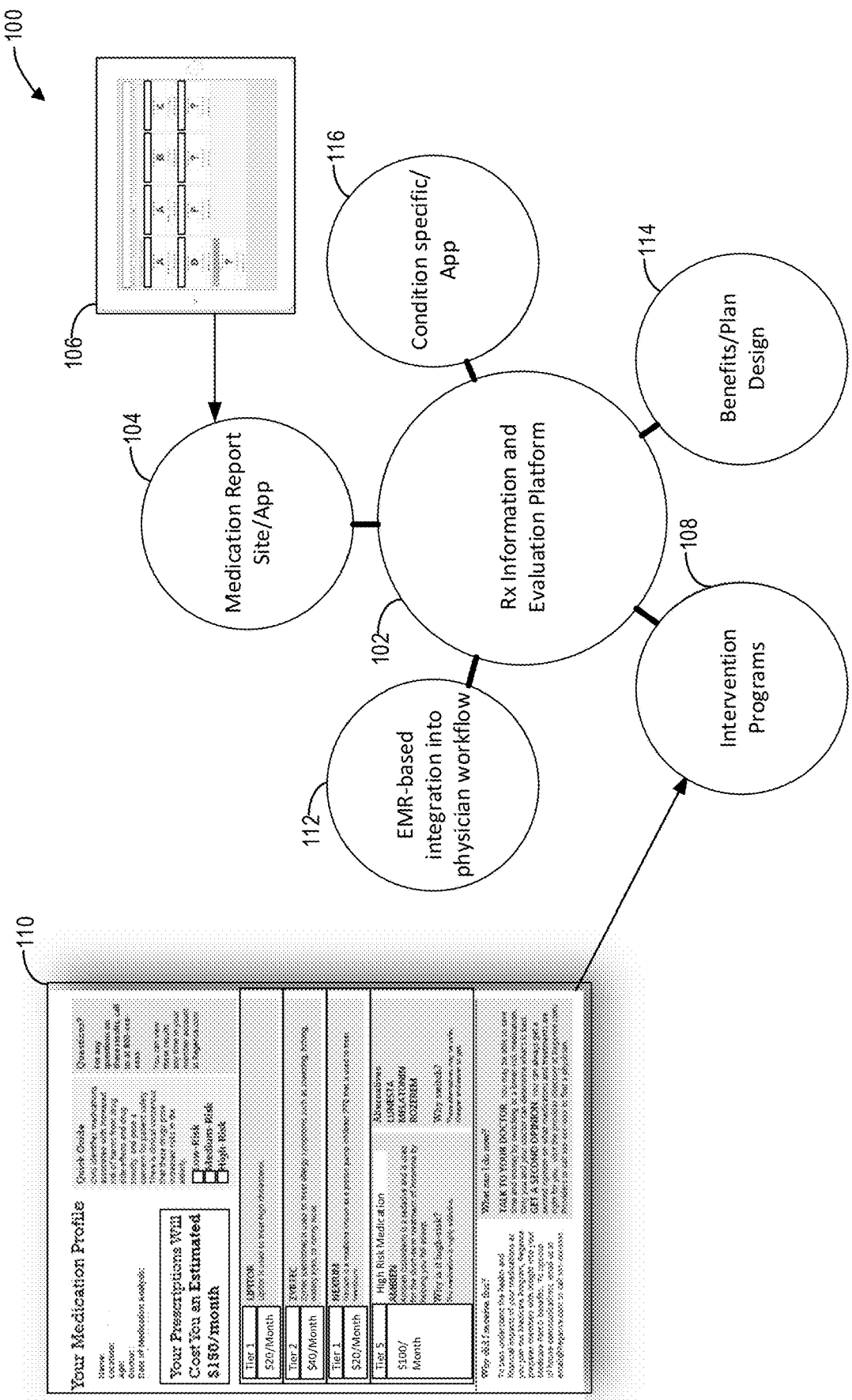
FIG. 1 shows a high-level illustration of an example online health care platform.

The following description relates to systems and methods for improving the transparency of the medication selection process. When selecting a medication, a user may access a healthcare platform through a user device such as a phone, tablet, computer, etc., as shown in FIG. 2. The healthcare platform may include a server in wireless communication with the user device as shown in FIG. 1, which may allow a user, to search for, compare, and purchase medications. A user may input medical and non-medical information into a user profile via the user device. Non-medical information may include a user's preferences, hobbies, interests, lifestyle, work conditions, etc. A user's profile information may be stored on the server in wireless communication with the user device. When searching for a medication, a user may first search for medications on their user device via a search display screen such as that shown in FIG. 8A. The server may contain a logic subsystem which may be configured to perform a method such as the example method of FIGS. 3A and 3B, to carry out the medication search requested by the user. Specifically, the server may search from one or more databases on one or more remote servers for information regarding medications used to treat the user's medical condition. Specifically, the method may include searching and evaluating scientific literature such as clinical studies involving a particular medication. As described in the example methods of FIGS. 4A, 4B, and 5, the results from the scientific literature, and the accuracy of those results may be assessed to determine the relevancy and importance of the study results. Based on the results of the studies, a user personalized grade may then be assigned to the medication as described in the example method shown in FIG. 6, which may be based both on the scientific studies and the information stored in the user's profile. The user personalized grade a medication receives may be indicative of its predicted effectiveness in treating the medical condition, as well as its safety concerns, and health risks. Other information regarding the medication may also be gathered such as the predicted cost, side effects, care provider recommendations, and user reviews of the medication. After gathering and analyzing relevant information relating to one or more medications, the medication information may be presented to a user, as described in the example method shown in FIG. 7.

In response to the user request for a medication search, a list of medications used to treat the user's medical condition may be provided. Medications may be displayed to a user via a user interface on the user device such as a touch screen, LCD screen, etc. As shown in FIGS. 8B, 8F, and 8G the display may include relevant information about each medication option such as its user personalized grade, cost factor, prescription evidence data, and secondary technical effects. Thus, the user may be able to compare various medications based on their cost, effectiveness, user reviews, side effects, etc. The user may then be able to quickly narrow down their search to a subset of the initially presented medications. After selecting a subset of the initially presented medications, the user may be presented with a display which allows for the comparison of the user selected medications as shown in the example display of FIG. 8C. After further narrowing their search, a user may select a single medication and receive even more information about the medication, such as links to the scientific literature used to estimate the effectiveness of the medication as shown in FIG. 8D.

A user and a user's care provider may have access to the user's profile through the healthcare platform. A care provider may include a user's medical doctor, specialist, nurse practitioner, physician's assistant, etc. The user profile, may contain current information about the user's medications as shown in FIG. 8E. A user may be provided with a list of current medications, the cost of each medication, an intended use for each medication, and an overall estimated cost for all current medications. The user's care provider may intervene and notify the user if one or more of the medications pose a serious health risk to the user.

As such, the systems and methods provided herein may provide additional advantages to previous attempts to address the transparency of the medication selection process. First, the effectiveness of medications for users may be increased while at the same time the cost may be decreased. Second, due to the improved transparency of the user interface used for selecting medications, the time a user spends selecting and purchasing a medication may be reduced. Third, the safety and health of a user may be increased by providing intervention strategies when a user selects a medication that could pose a serious health risk.

FIG. 1 illustrates an example of a high-level representation of a healthcare platform. The healthcare platform comprises a system for evaluating medication options via an interactive software environment to help users make informed healthcare decisions. Thus, the healthcare platform may increase the transparency of healthcare options available to users. Additionally, the healthcare platform may synchronize the entire process of researching, selecting, and purchasing medications into a single user interface. In other words, users may search, compare, and purchase medications all on one health platform. Further, user may compare medications by what factor is most important to them in a medication: its cost, effectiveness, side effects, etc.

An example health platform 100, shown in FIG. 1, may comprise a information and evaluation platform 102, a Consumer Reports style medication report site and/or application 104, condition specific online applications 116, a benefits and/or plan design 114, intervention programs 108, and an electronic medical records (EMR) based integration into physician workflow component 112. For example, a user may first search for medications based on their specific condition on the condition specific online application or site 116. Next, after the platform 102 gathers and evaluates information relating to the medications associated with the user's conditions, users may be presented the various medication options and a side-by-side comparison tool 106 for comparing and evaluating the medication options. Information pertaining to the medication options, such as their cost factor, user personalized grade, secondary technical effects, care provider recommendations, prescription experience data, etc., may be presented side-by-side to the user on a single interface.

For the purposes of simplifying terms used in this disclosure, a cost factor may relate to an estimated cost of a medication. The cost factor may be the estimated cost of a medication before a deductible. In another example, the cost factor may be the estimated cost of a medication after a deductible. In other examples, the cost factor may not be the exact cost of the medication to the user out of pocket. Secondary technical effects of a medication may include side effects of the medication as determined based on scientific research and literature of studies of the medication. Prescription experience data may include comments, reviews, and other forms of feedback from other users and/or patients who had previous experience with the medication. The user personalized grade may be a user personalized grade calculated for a medication based on both scientific literature and user information as will be explained in greater detail in the methods below with reference to FIGS. 3-6.

Further, the benefits and or plan design 114 may allow a user to select a medication and obtain information about its cost, both before and after a deductible. As will be explained in greater detail below with reference to FIG. 8G, if a user chooses a medication that may be a health risk to the user, the user may be sent a message explaining the potential heal risks associated with taking the chosen medication. In another example, the healthcare platform 100 may prevent a user from purchasing a medication that poses more than a threshold amount of health risk to the user.

As part of the intervention programs 108, a patient profile 110 may be presented to the user displaying their medications, their costs, and their risk factors. If it is determined by the platform 102 that one or more of the medications taken by the patient poses more than a threshold amount of risk to the patient, the patient may be alerted.

Thus, platform 100 may allow users to more easily sort through and evaluate their medication options, due to the increased transparency and functionality of the platform 100. Specifically, and as elaborated in greater detail below with reference to FIGS. 8B-8G, users may compare medication by an assigned user personalized grade. In one example the user personalized grade may be a letter grade such as "A," "B," "C," etc. In another example, the user personalized grade may be a number on a particular scale (e.g., a number from 1 to 10). The user personalized grade may be based on evidence of the efficacy and safety of the medication as reported in peer reviewed literature and information provided to the FDA. In one example, links to the peer reviewed literature may be provided to the user. User reviews such as individual user feedback on their unique experience with medications may be aggregated to provide a crowd-sourced rating. Additionally, a user's care provider database may be updated to provide a current list of all medications the user is taking. Users may therefore be provided with a more efficient means for comparing and evaluating their medication options. Further, the safety and efficacy of medications in treating medical conditions may be improved while at the same time the cost to the user may be reduced.

Figure 2A:
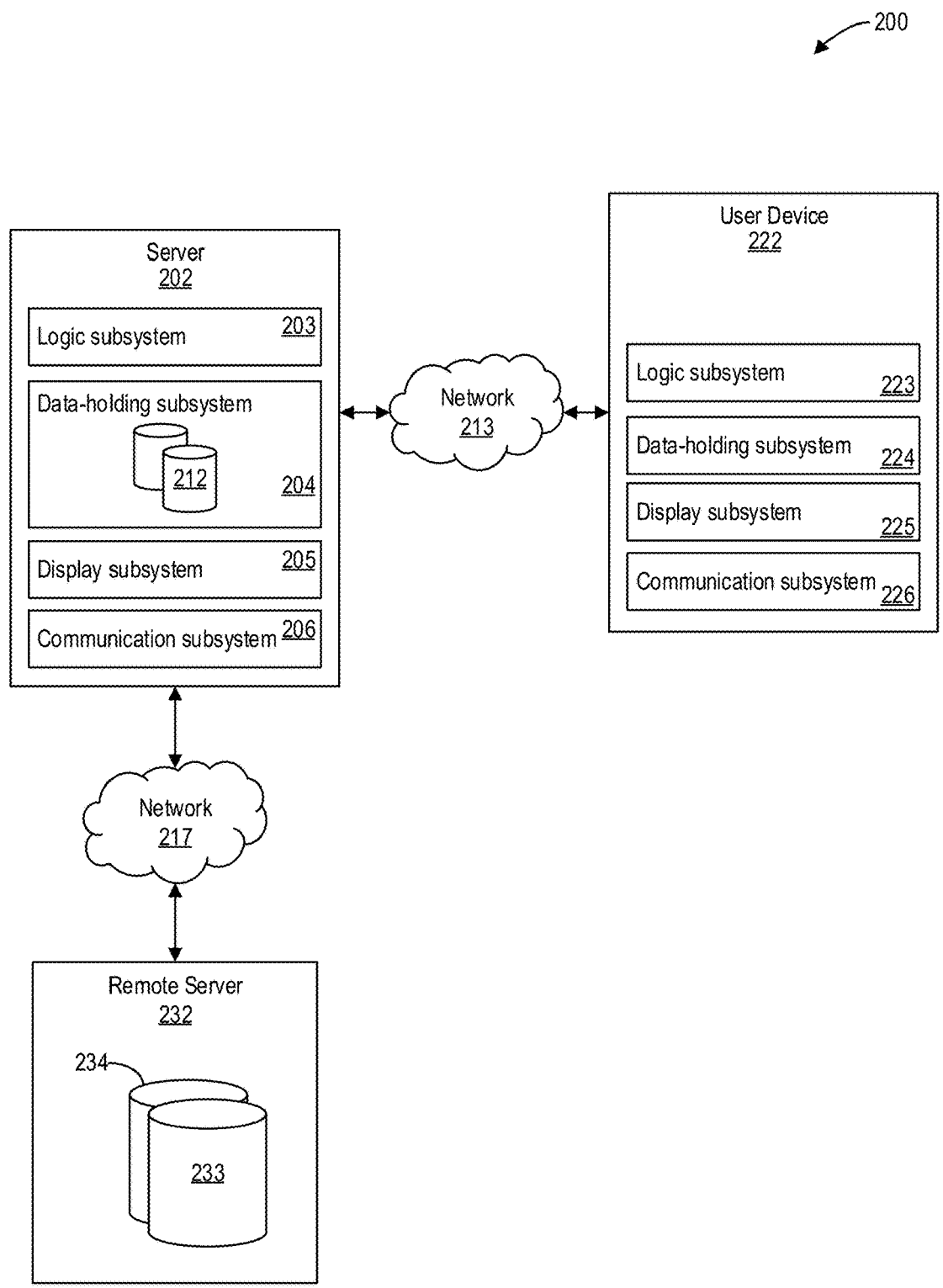
FIG. 2A illustrates an overview of an exemplary computing environment according to an embodiment.

FIG. 2A illustrates an example computing environment 200 in accordance with the current disclosure. In particular, computing environment 200 includes a server 202, a user device 222, a remote server 232, and networks 213 and 217. However, not all of the components illustrated may be required to practice the invention. Variations in the arrangement and type of the components may be made without departing from the spirit or scope of the invention.

Server 202 may be a computing device configured to: generate a user personalized grade for a medication, and calculate medication costs from claims data. In one example, the user personalized grade may be related to the predicted effectiveness of the medication. Further the user personalized grade may be based on one or more of available scientific research, clinical studies, patient reviews, care provider recommendations, etc. In different embodiments, server 202 may take the form of a mainframe computer, server computer, desktop computer, laptop computer, tablet computer, home entertainment computer, network computing device, mobile computing device, mobile communication device, gaming device, etc.

Server 202 includes a logic subsystem 203 and a data-holding subsystem 204. Server 202 may optionally include a display subsystem 205, communication subsystem 206, and/or other components not shown in FIG. 2A. For example, server 202 may also optionally include user input devices such as keyboards, mice, game controllers, cameras, microphones, and/or touch screens.

Logic subsystem 203 may include one or more physical devices configured to execute one or more instructions. For example, logic subsystem 203 may be configured to execute one or more instructions that are part of one or more applications, services, programs, routines, libraries, objects, components, data structures, or other logical constructs. Such instructions may be implemented to perform a task, implement a data type, transform the state of one or more devices, or otherwise arrive at a desired result.

Logic subsystem 203 may include one or more processors that are configured to execute software instructions. Additionally or alternatively, the logic subsystem 203 may include one or more hardware or firmware logic machines configured to execute hardware or firmware instructions. Processors of the logic subsystem 203 may be single or multi-core, and the programs executed thereon may be configured for parallel or distributed processing. The logic subsystem 203 may optionally include individual components that are distributed throughout two or more devices, which may be remotely located and/or configured for coordinated processing. For example, the logic subsystem 203 may include several engines for processing and analyzing data. These engines may include a test evaluator engine, user comment engine, user review engine, user feedback engine, etc. These engines may be wirelessly connected to one or more databases for processing data from the databases. One or more aspects of the logic subsystem 203 may be virtualized and executed by remotely accessible networked computing devices configured in a cloud computing configuration.

Data-holding subsystem 204 may include one or more physical, non-transitory devices configured to hold data and/or instructions executable by the logic subsystem 203 to implement the herein described methods and processes. When such methods and processes are implemented, the state of data-holding subsystem 204 may be transformed (for example, to hold different data).

Data-holding subsystem 204 may include removable media and/or built-in devices. Data-holding subsystem 204 may include optical memory (for example, CD, DVD, HD-DVD, Blu-Ray Disc, etc.), and/or magnetic memory devices (for example, hard drive disk, floppy disk drive, tape drive, MRAM, etc.), and the like. Data-holding subsystem 204 may include devices with one or more of the following characteristics: volatile, nonvolatile, dynamic, static, read/write, read-only, random access, sequential access, location addressable, file addressable, and content addressable. In some embodiments, logic subsystem 203 and data-holding subsystem 204 may be integrated into one or more common devices, such as an application-specific integrated circuit or a system on a chip.

It is to be appreciated that data-holding subsystem 204 includes one or more physical, non-transitory devices. In contrast, in some embodiments aspects of the instructions described herein may be propagated in a transitory fashion by a pure signal (for example, an electromagnetic signal) that is not held by a physical device for at least a finite duration. Furthermore, data and/or other forms of information pertaining to the present disclosure may be propagated by a pure signal.

When included, display subsystem 205 may be used to present a visual representation of data held by data-holding subsystem 204. As the herein described methods and processes change the data held by the data-holding subsystem 204, and thus transform the state of the data-holding subsystem 204, the state of display subsystem 205 may likewise be transformed to visually represent changes in the underlying data. Display subsystem 205 may include one or more display devices utilizing virtually any type of technology. Such display devices may be combined with logic subsystem 203 and/or data-holding subsystem 204 in a shared enclosure, or such display devices may be peripheral display devices.

When included, communication subsystem 206 may be configured to communicatively couple server 202 with one or more other computing devices, such as user device 222 and/or remote server 232. Communication subsystem 206 may include wired and/or wireless communication devices compatible with one or more different communication protocols. As non-limiting examples, communication subsystem 206 may be configured for communication via a wireless telephone network, a wireless local area network, a wired local area network, a wireless wide area network, a wired wide area network, etc. In some embodiments, communication subsystem 206 may allow server 202 to send and/or receive messages to and/or from other devices via a network such as the public Internet. For example, communication subsystem 206 may communicatively couple server 202 with user device 222 via network 213 and/or server 232 via network 217. In some examples, network 213 may be the public Internet. Furthermore, network 217 may be regarded as a private network connection and may include, for example, a virtual private network or an encryption or other security mechanism employed over the public Internet. In some examples, network 213 and network 217 may be the same network.

Computing environment 200 may include one or more devices operated by users, such as user device 222. User device 222 may be any computing device configured to access a network such as network 213, including but not limited to a personal computer, a laptop, a smartphone, a tablet, and the like.

User device 222 includes a logic subsystem 223 and a data-holding subsystem 224. User device 222 may optionally include a display subsystem 225, communication subsystem 226, and/or other components not shown in FIG. 2A. For example, user device 222 may also optionally include user input devices such as keyboards, mice, game controllers, cameras, microphones, and/or touch screens.

Logic subsystem 223 may include one or more physical devices configured to execute one or more instructions. For example, logic subsystem 223 may be configured to execute one or more instructions that are part of one or more applications, services, programs, routines, libraries, objects, components, data structures, or other logical constructs. Such instructions may be implemented to perform a task, implement a data type, transform the state of one or more devices, or otherwise arrive at a desired result.

Logic subsystem 223 may include one or more processors that are configured to execute software instructions. Additionally or alternatively, the logic subsystem 223 may include one or more hardware or firmware logic machines configured to execute hardware or firmware instructions. Processors of the logic subsystem 223 may be single or multi-core, and the programs executed thereon may be configured for parallel or distributed processing. The logic subsystem 223 may optionally include individual components that are distributed throughout two or more devices, which may be remotely located and/or configured for coordinated processing. One or more aspects of the logic subsystem 223 may be virtualized and executed by remotely accessible networking computing devices configured in a cloud computing configuration.

Data-holding subsystem 224 may include one or more physical, non-transitory devices configured to hold data and/or instructions executable by the logic subsystem 223 to implement the herein described methods and processes. When such methods and processes are implemented, the state of data-holding subsystem 224 may be transformed (for example, to hold different data).

Data-holding subsystem 224 may include removable media and/or built-in devices. Data-holding subsystem 224 may include optical memory (for example, CD, DVD, HD-DVD, Blu-Ray Disc, etc.), and/or magnetic memory devices (for example, hard drive disk, floppy disk drive, tape drive, MRAM, etc.), and the like. Data-holding subsystem 224 may include devices with one or more of the following characteristics: volatile, nonvolatile, dynamic, static, read/write, read-only, random access, sequential access, location addressable, file addressable, and content addressable. In some embodiments, logic subsystem 223 and data-holding subsystem 224 may be integrated into one or more common devices, such as an application-specific integrated circuit or a system on a chip.

When included, display subsystem 225 may be used to present a visual representation of data held by data-holding subsystem 224. As the herein described methods and processes change the data held by the data-holding subsystem 224, and thus transform the state of the data-holding subsystem 224, the state of display subsystem 225 may likewise be transformed to visually represent changes in the underlying data. Display subsystem 225 may include one or more display devices utilizing virtually any type of technology. Such display devices may be combined with logic subsystem 223 and/or data-holding subsystem 224 in a shared enclosure, or such display devices may be peripheral display devices.

When included, communication subsystem 226 may be configured to communicatively couple user device 222 with one or more other computing devices, such as server 202. Communication subsystem 226 may include wired and/or wireless communication devices compatible with one or more different communication protocols. As non-limiting examples, communication subsystem 226 may be configured for communication via a wireless telephone network, a wireless local area network, a wired local area network, a wireless wide area network, a wired wide area network, etc. In some embodiments, communication subsystem 226 may allow user device 222 to send and/or receive messages to and/or from other devices, such as server 202, via a network 213 such as the public Internet.

Similarly, remote server 232 may comprise a computing device communicatively coupled to server 202 via network 217. In some examples, the remote server 232 may include a plurality of remote servers, such as a claims server, medical database server, pharmacy server, etc., all coupled to server 202 via network 217. The one or more remote servers included in remote server 232 may each include one or more databases 233. Thus, in one example, remote server 232, may include one or more servers that contain one or more databases with raw medical data, where the raw medical data may include information regarding health care treatments, services, costs, and so on.

The remote server 232 may include a plurality of databases. For example, the remote server 232 may include one or more medication information databases 233, and a patient profile database 234. The patient profile database 234 may include information about a patient. Specifically, a patient may input their patient characteristics, information, preferences, medical history, etc., via the user device 222, and their information may be stored in the patient profile database 234 of the remote server 232.

Further, the medication databases 233 may include information about medications such as their cost, effectiveness, risk factors, etc. Thus, the medication databases 233 may include one or more of a medication database, clinical effectiveness database, user review database, cost database, risk database, etc.

Additionally, remote server 232 may include one or more study result database servers that contain one or more study result databases with raw scientific data, clinical study data, medical report data, published scientific study data, etc., which may include information regarding the effectiveness of health care treatments including, but not limited to, prescriptions medications, secondary technical effects of those medication, etc. The remote server 232 may further include one or more pharmacy servers that contain one or more claims databases with raw patient data, raw claims data, and so on. The remote server may additionally include one or more servers containing one or more patient experience databases with patient feedback and reviews for one or more medications. Thus the remote server 232 may include one or more servers each containing one or more databases that include information relating to scientific evidence and research on a plurality of health care treatments, the cost of said treatments, patient and user reviews of said treatments, side effects of said treatments, etc.

Thus server 202, user device 222, and remote server 232 may each represent computing devices which may generally include any device that is configured to perform computation and that is capable of sending and receiving data communications by way of one or more wired and/or wireless communication interfaces. Such devices may be configured to communicate using any of a variety of network protocols. For example, user device 222 may be configured to execute a browser application that employs HTTP to request information from server 202 and then displays the retrieved information to a user on a display. Example interfaces that may be delivered to user device 222 from server 202 in such a manner and displayed, for example, on display subsystem 225 are described further herein and with regard to FIGS. 8A-8G.

Server 202 may collect and process data from remote server 232 and from user device 222. A user may input personal information to the user device 222 such as their age, gender, ethnicity, etc., and any preferences they may have pertaining to medication options such as cost, side effects, accessibility, effectiveness, etc., of said medication options. User information may be transferred to server 202 via network 213, and may be stored in the data-holding subsystem 204 of the server 202. As explained above, in other examples, the user information may be stored in the patient profile database 234 of the remote server 232.

Server 202 may analyze the user information collected from user device 222 and/or patient profile database 234 of remote server 232, and medication information collected from the one or more medication information databases of remote server 232 using, for example, data analysis techniques and/or artificial intelligence techniques. For example, data collected from the one or more databases in remote server 232 may be analyzed to determine certain aspects of a particular medication, which may include one or more of the cost for the medication, a score for the medication, the effectiveness of the medication in treating a condition, etc. In one example, the user personalized grade of the medication may be based on data retrieved from the study result database. The personalized user personalized grade of the medication may be based on the effectiveness of the medication in treating a particular medical condition. The effectiveness may be based on scientific, clinical, and or medical studies, medical doctor recommendations, and user reviews. As such, the test evaluator engine may retrieve information regarding a medication from one or more databases such as the study result database, and manipulate and evaluate the data together with the information obtained about the user from the user profile, to calculate a user personalized grade for the medication.

In other examples, the user personalized grade may alternatively or additionally be based on side effects of the medication, cost of the medication, user reviews of the medication, etc. In still further examples, the medication score may be based on one or more of a combination of the aforementioned parameters. The data received from the remote server 232 to determine a score of the medication may be data collected from patients as part of a scientific, clinical, and/or medical study. Additionally, the data used to determine the score of a medication may be data collected from any person taking the particular medication and submitting feedback either via the Internet, or written correspondence. Further, server 202 may estimate the cost of a particular medication, or healthcare treatment based on collected data from the remote server 232 pertaining to medical claims.

However, aspects of a particular medication may not be the same for all users, and may be different depending on the user. As an example, the cost of a particular medication to a user may depend on the user's insurance. As another example, the effectiveness of a medication may depend on the user's characteristics, traits, and preferences. A given medication may be more effective for males than females, or for ages 50 and above than 30 and under, etc. Thus, when analyzing the medication information collected from the one or more medication information databases 233 of remote server 232, server 202 may determine the effectiveness, score, and cost of a particular medication, based on the user information collected from user device 222 and/or patient profile database 234 of remote server 232. As a result, analysis of medication information may be personalized for each user as will be elaborated below with reference to FIGS. 3A-3B. Thus, by taking into account various characteristics of a particular user, the accuracy of medication and healthcare information presented to the user may be increased. Said another way, using information provided by the user via user device 222 may be used to increase the accuracy of the score, effectiveness, cost, etc., of a medication for a particular user. Systems and methods for determining medication scores and effectiveness are described further herein with regard to FIGS. 3A-7.

Analysis of medication data may further provide an overview of services and costs associated with particular health conditions and treatments for similar users. Various factors such as the insurance coverage, deductible, benefits, etc., may be used in determining the cost of a medication to a particular patient or user. Server 202 may include one or more databases 212 in data-holding subsystem 204 for storing processed claims data, and processed medication score data. As such, server 202 may be capable of processing claims and executing purchases of medication responsive to input from the user device 222. Thus, remote server 232 may include one or more servers and/or databases linked to one or more financial institutions, pharmacies, insurance companies, care providers, etc. As such, server 202, may be able to process purchase requests, payments and claims responsive to a user input through user device 222.

Figure 2B:
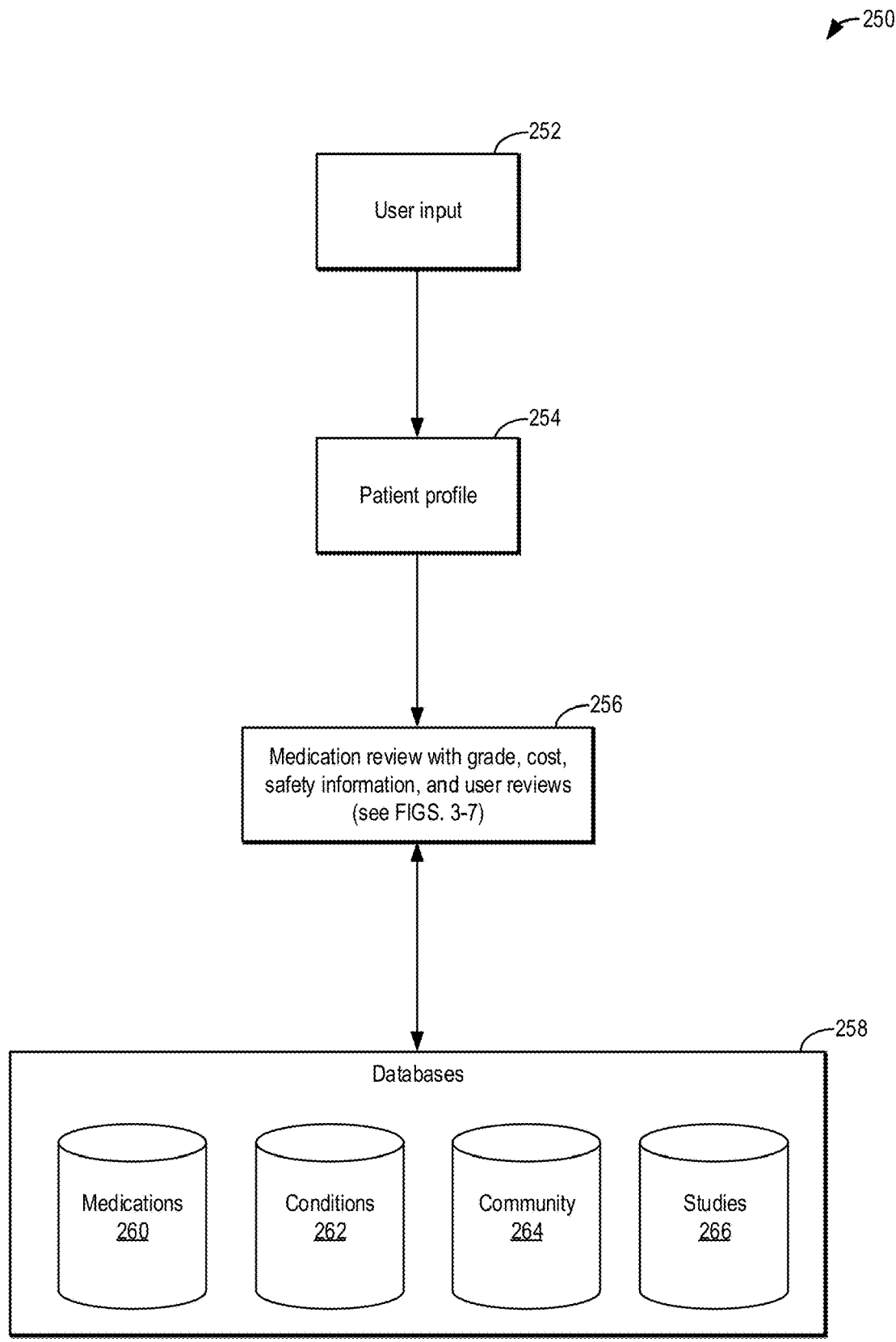
FIG. 2B illustrates another example computing environment.

FIG. 2B shows another embodiment of a computing environment 250 that may be used in accordance with the present disclosure. Specifically, computing environment 250 may be an example computing environment of computing environment 200 from FIG. 2A.

At 252, a user may input information into the computing environment 200. Specifically, at 252, a user may provide information to a server (e.g., server 202 from FIG. 2A) via a user interface and network connection (e.g., network connection 213 from FIG. 2A). The user input may include information and preferences pertaining to the user. In one example, the user input may include general personal and medical information about the user, such as medication the user is currently taking, past and/or current medical conditions, medical history, gender, age, ethnicity, medication usage, travel history, etc. In other examples, the user may additionally or alternatively input non-medical information such as preferences, hobbies, interests, lifestyle, work conditions, etc. In some examples, the user preferences may include preferences regarding the selection of medications, such as the relative importance of the cost, effectiveness, side effects, etc., of various medication options. Thus, in some examples at 304, the user may update information in their patient profile pertaining to their current living and medical conditions. However, in other examples, a user may input information regarding a new medical condition, and may further request information about potential medications to treat said condition.

At 254, information input by the user at 252 may be stored in a patient profile. In one example, the patient profile may be stored in a data-holding system (e.g., data-holding subsystem 204 from FIG. 2A). Thus, a user may access and update their patient profile through the network connection. Additionally a user may input a new condition and request for information regarding medications used in treating said condition.

At 256, a server, (e.g., server 202 from FIG. 2A) may generate a medication review that includes one or more of a user personalized grade, cost, safety information, user review, and care provider recommendations of various medications. In one example, the medication review generated at 256 may pertain to specific medical condition input by the user at 252. As such, the medication review may include a review of medication used in treating a particular medical condition. For example, if a user requests information about medication options for specific condition at 252, the computing environment 250 may generate the medication review at 256 specifically for medications pertaining to the user's condition. In another example, the computing environment 250 may generate a medication review for any medical condition the user inputs at 252. Thus, even if a user does not request for a medication review at 252, the computing environment may automatically generate a medication review for any and all conditions input and/or stored in the patient profile.

To generate the medication review at 256, the server may communicate with one or more databases 258 (e.g., databases 233 from FIG. 2A) via a network connection (e.g., network 217 from FIG. 2A). The databases may be included in one or more remote servers (e.g., remote server 232 from FIG. 2A). The databases may comprise one or more of a medications database 260, conditions database 262, community database 264, and studies database 266. The medication database 260, may include information regarding medications that are available on a healthcare marketplace. These medications in the medication database 260 may include over-the-counter medication and prescription medications. The conditions database 262 may include a list and information regarding known medical conditions, such as diseases, cancers, infections, etc. The community database 264 may include reviews of medications from patients, and other users of said medications. The studies database 266 may include information from peer reviewed and published literature. Specifically, the studies database 266 may include information and results from clinical studies, reporting the efficacy of one or more medications in treating a particular medical condition. As will be explained in greater detail with reference to FIGS. 3-7, the computing environment 250, may use information gathered from the one or more databases 258 to generate the medication review at 256.

Thus, a server, in communication with one or more remote servers, each having one or more databases, may collect information regarding a condition and medications for treating said medical condition to generate a review for said medication. The server may contain one or more engines with micro-chip processors for analyzing the data received from the one or more databases. For example, the server may comprise a test evaluator engine for generating the user personalized grade for each medication. The server may additionally comprise one or more of a user comment engine, user review engine, secondary technical effect database, etc. In some examples, the medication review may be stored in a server at 256. In other examples, the medication review may be presented to a user via a user interface. In still further examples, the medication review may be presented to a user via a request from the user via a user interface.

Figure 4A:
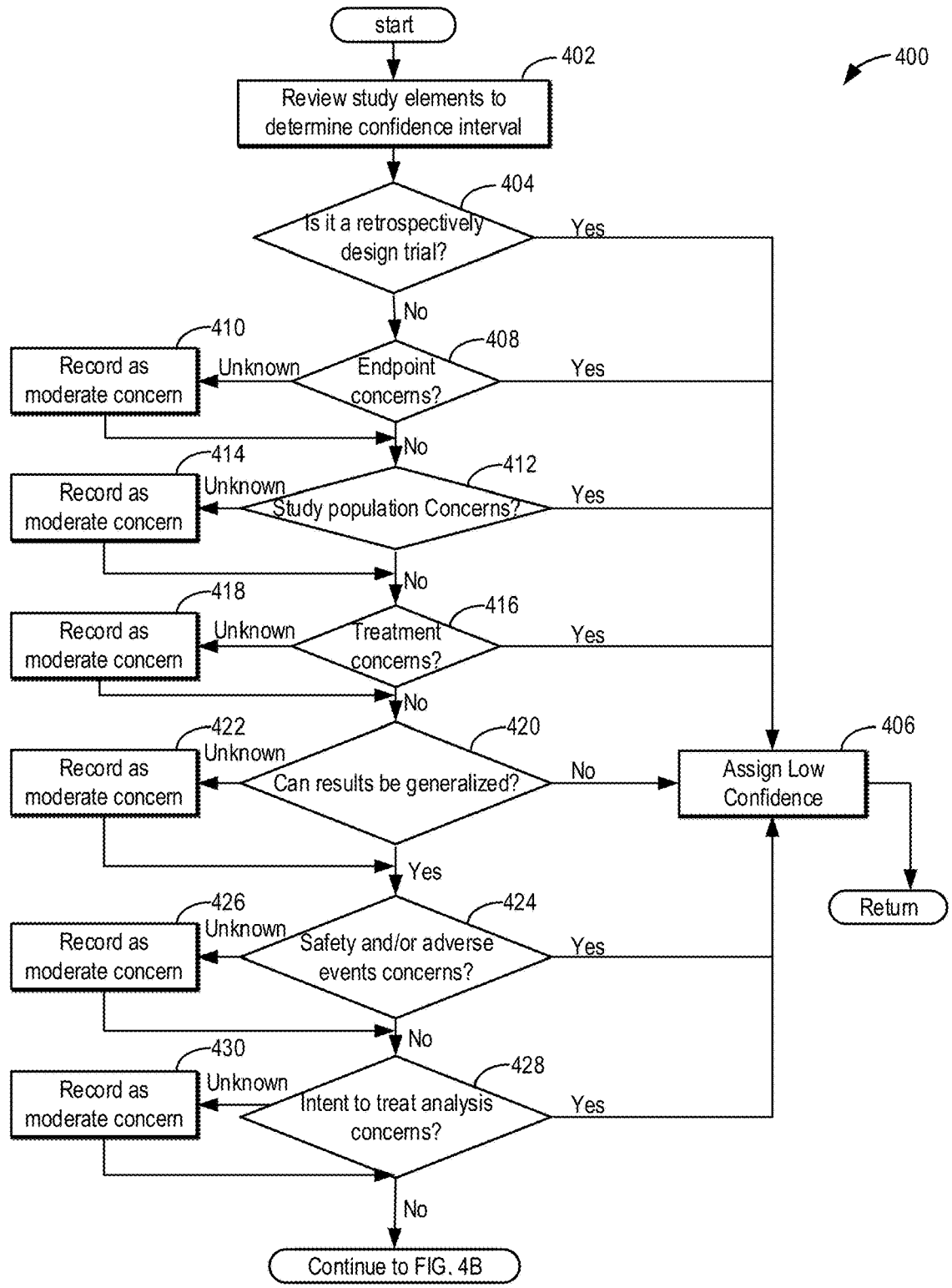
FIG. 4A shows a flow chart of an example method for appraising an individual medical study.
Figure 4B:
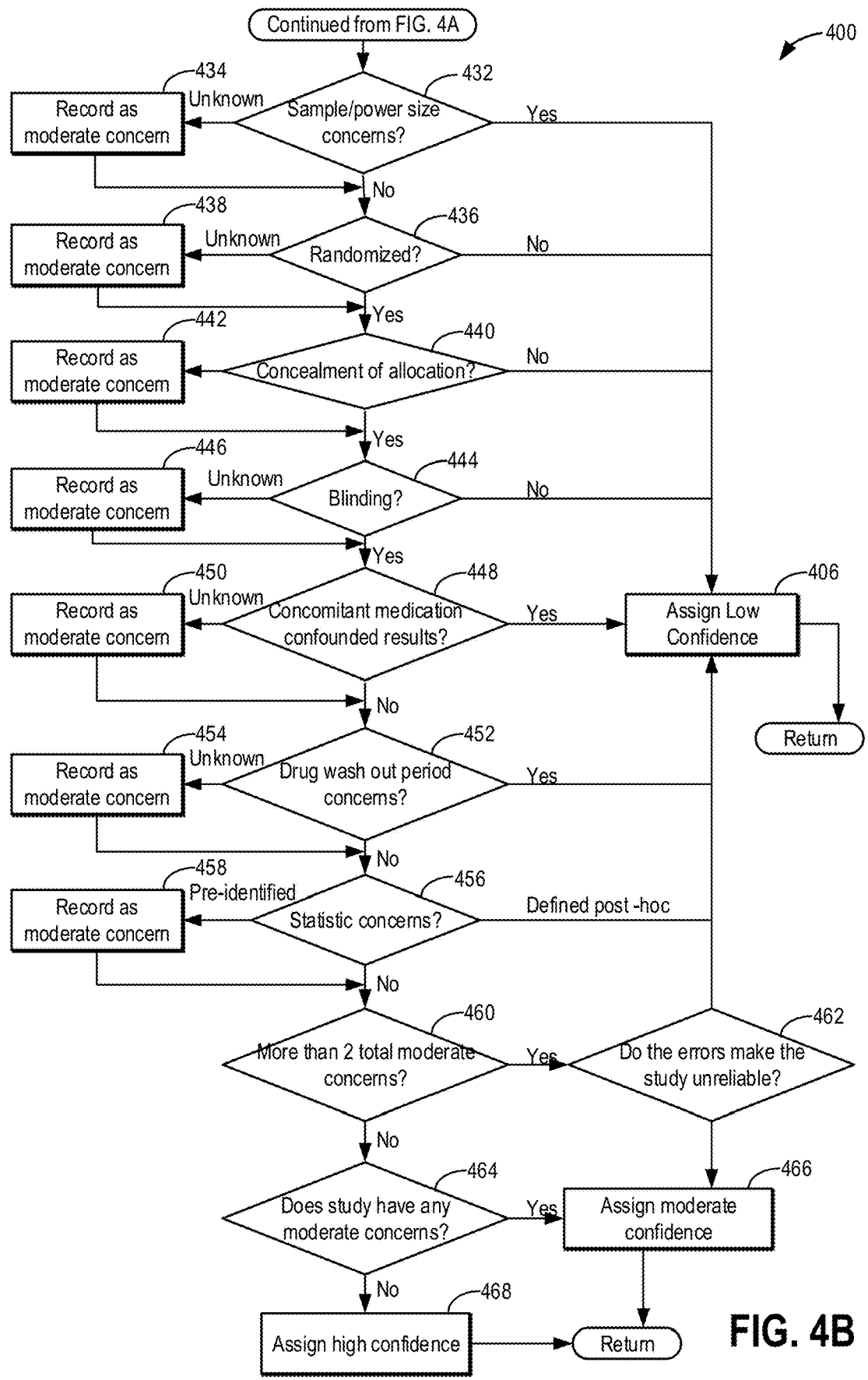
FIG. 4B shows a continuation of the example method for appraising an individual medical study from FIG. 4A.
Figure 5:
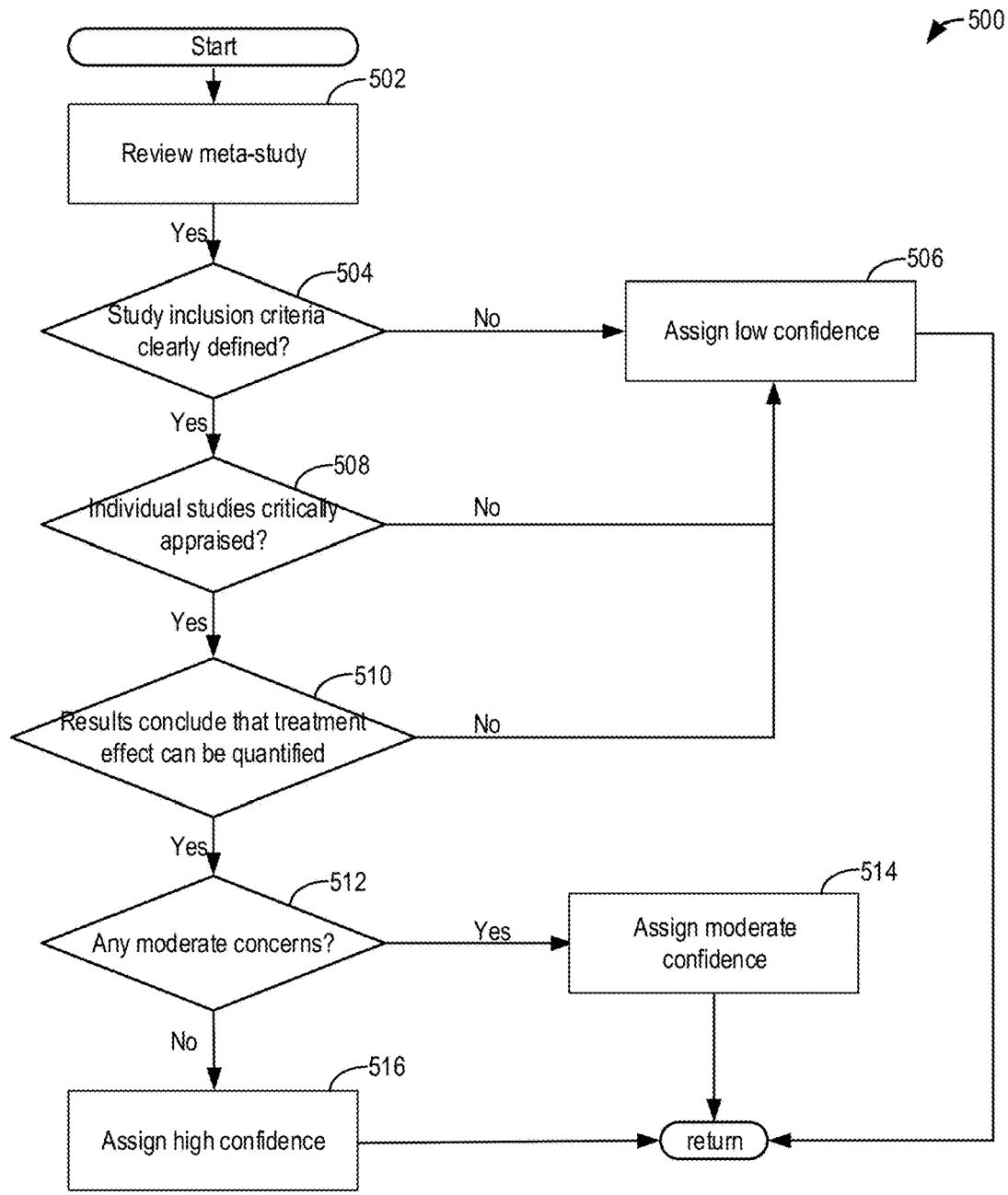
FIG. 5 shows a flow chart of an example method for appraising a meta-analysis medical study.
Figure 6:
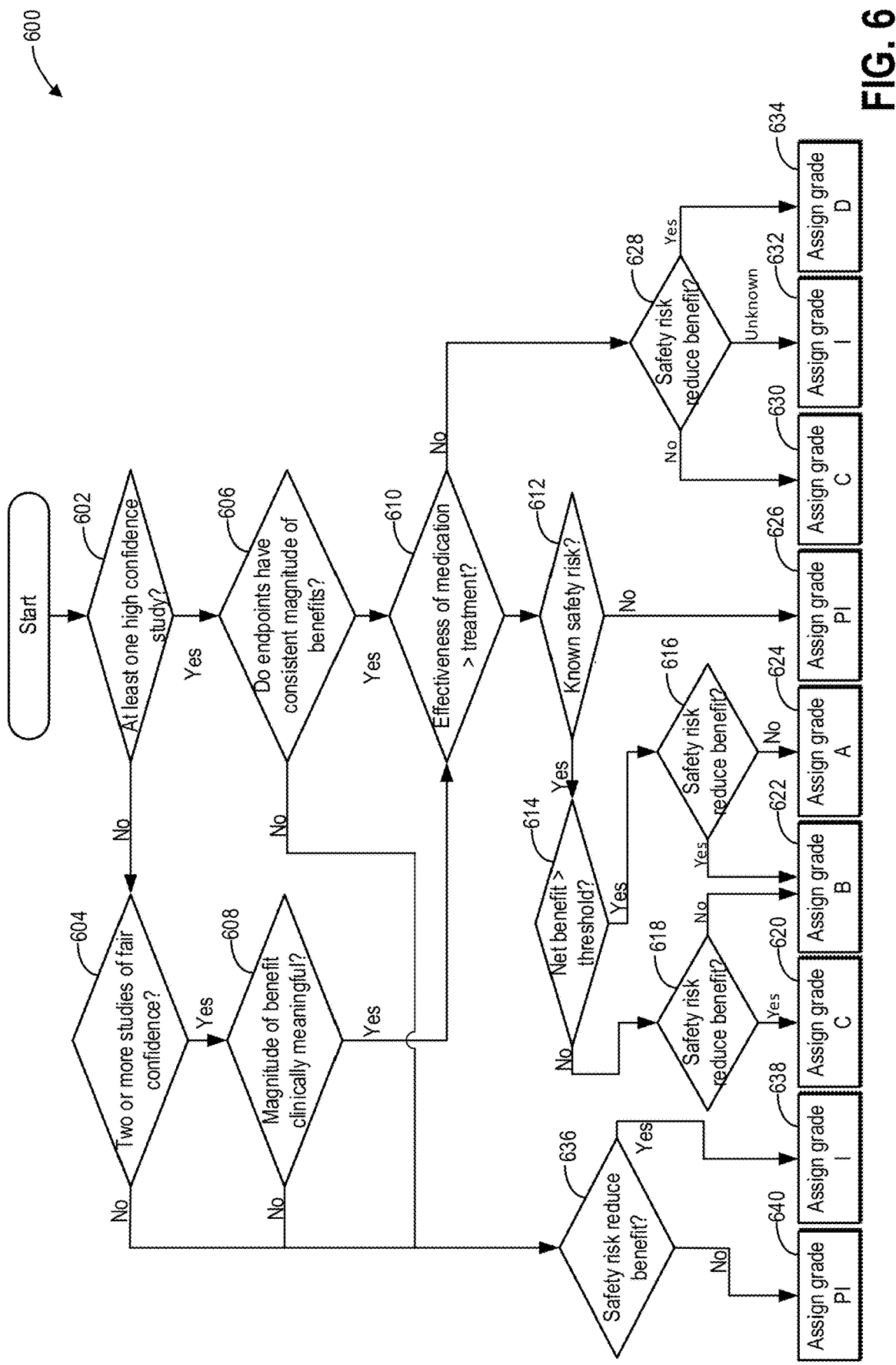
FIG. 6 shows a flow chart of an example method for appraising a medication in treating a particular medical condition.

FIGS. 3-6 show several methods for evaluating the effectiveness and safety of a medication in treating a particular medical condition. As such, methods 3-6 may be executed by a computer and/or server with a logic system capable of executing computer readable instructions such as server 202 described above with reference to FIG. 2A. Thus, in one embodiment, the methods described below in FIGS. 3-6 may be executed by the server (e.g., server 202 from FIG. 2A), the server being part of a wirelessly connected computing environment (e.g., computing environment 200 from FIG. 2A). The methods may include searching a database of scientific literature (e.g., databases 233 from FIG. 2A) for studies specifically concerning the medication. In one example the medication may be medication used in treating a medical condition input by a user via a user device (e.g., user device 222 from FIG. 2A). Thus, one or more of the methods in FIGS. 3-6 may be employed in response to a request from a user via the user device to search for medication used to treat a particular medical condition. As such, the methods in FIGS. 3-6 may be used to evaluate the effectiveness, safety, risks, etc., of a particular medication in treating a given medical condition. FIGS. 3A-3B show a method for grading a medication based on evaluating one or more pieces of scientific literature. Various subroutines of the method described in FIGS. 3A-3B may be executed in the method described in FIGS. 4-6. Specifically, the method shown in FIGS. 3A-3B, may include evaluating the confidence of the results of one or more studies involving a medication, which may be described in greater detail in the methods included in FIGS. 4 and 5. Further, the method shown in FIGS. 3A-3B may include assigning a user personalized grade to a medication based on its effectiveness, safety, health risks, etc. FIG. 6 may include an example method for assigning a user personalized grade to a medication.

Figure 3A:
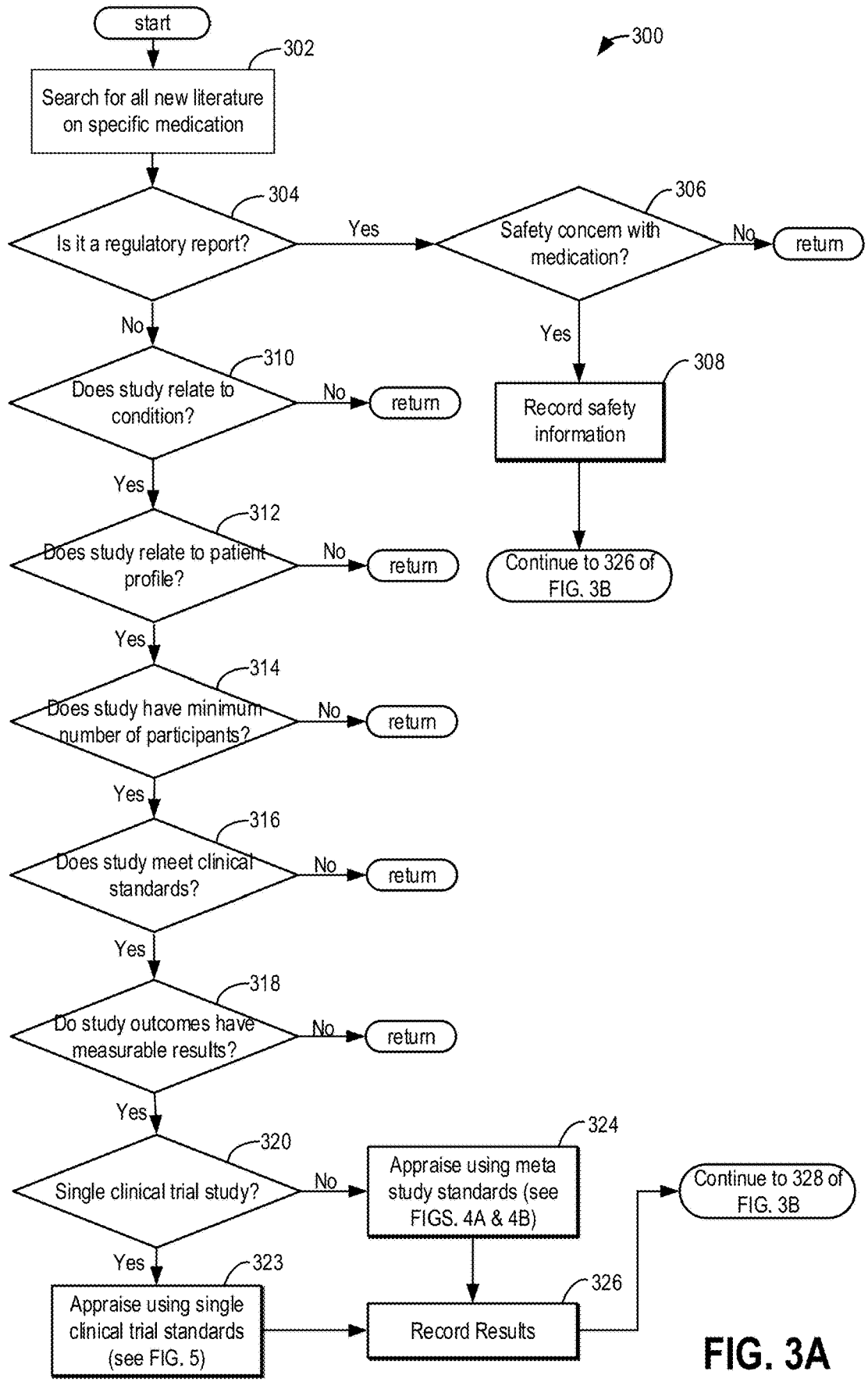
FIG. 3A shows a flow chart of an example method for appraising medications.
Figure 3B:
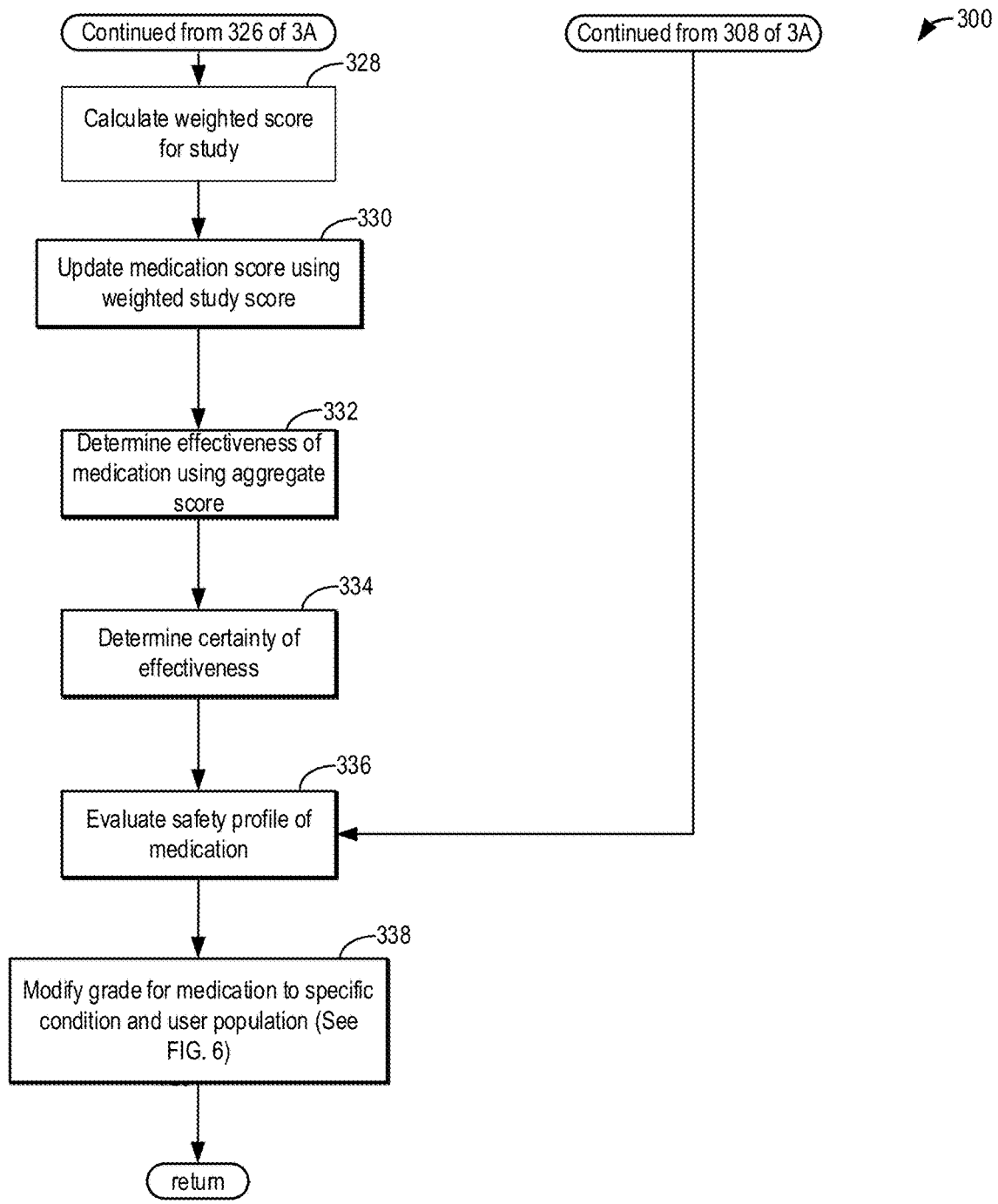
FIG. 3B shows a continuation of the example method for appraising medications from FIG. 3A.

FIGS. 3A-3B shows a flow chart of an example method 300 for evaluating a medication. Specifically, method 300 may comprise grading medications based on available scientific literature. The scientific literature may include clinical studies, meta-analyses, systematic reviews of clinical studies, research studies, peer reviewed literature, FDA approved studies, etc. In other words, method 300 may involve determining the efficacy of a medication in treating a particular medical condition. Specifically, a user personalized grade may be assigned to a medication, the user personalized grade being indicative of the effectiveness of the medication in treating a particular medication. In other examples, method 300 may comprise updating the user personalized grade assigned to a particular medication based on new available scientific literature. Thus, method 300 may involve grading various medications used to treat the same medical condition. The user personalized grades assigned to the medication may allow for improved transparency and ease of comparison between different medication options. Further, the user personalized grade assigned to a medication may be based on its predicted effectiveness in a patient based on information about that patient. Thus, the user personalized grade assigned to a given medication may be different depending on the patient and their specific personal, medical, and non-medical information. As such, method 300 allows for improved accuracy of the predicted effectiveness of a medication in treating a medical condition. Said another way, the predicted user personalized grade and/or effectiveness of a medication may be user-specific to offer improved medication suggestions. It is important to note that method 300 may be executed in response to a request from a user. For example, a user may input a search for a particular medical condition on a user device (e.g., user device 222 from FIG. 2A). In response to the request from the user, a server (e.g., server 202 from FIG. 2A) in communication with the user device via a network (e.g., network 213) may execute method 300. Thus, method 300 may additionally include assigning user personalized grades to various medications used to treat a particular medical condition input by a user.

Instructions for carrying out method 300 may be stored in the memory of a computer and/or server (e.g., data holding subsystem 204 of server 202 from FIG. 2A). As such, method 300 may be carried out by a logic system (e.g., logic subsystem 203 from FIG. 2A) of the computer and/or server.

Method 300 begins at 302 by searching for all new literature on a specific medication. In one example, the method 300 at 302 may involve searching all scientific literature for a specific medication. In other examples, the method 300 at 302 may only involve searching scientific literature for a specific medication within a threshold amount of time from the current time (e.g., within the last one year, 5 years, 3 months, etc.). The scientific literature may be drawn from one or more data-holding systems or study result databases (e.g., databases 233 from FIG. 2A). It is important to note that method 300 may repeat itself multiple times. In other examples it may run continuously. As such the searching for scientific literature may comprise only searching for scientific literature within a time period, the time period dictated by the time since the most recent search. As such, the method 300 at 302 may only search for scientific literature published since the most recent execution of method 300 for the given specific medication. In the following description, a piece of scientific literature may also be herein referred to as a study.

Continuing to 304, the method 300 may involve determining if the scientific literature uncovered at 302 is a regulatory report. If the scientific literature pertaining to the specific medication is a regulatory report, method 300 may proceed to 306 and determine if there is a safety concern with the medication. A safety concern may include a potential health risks, negative side effects, addictiveness of the medication, etc. In response to determine that there are no safety concerns with the medication at 306, the method 300 may return. However, if at 306, a safety concern with the medication is identified, method 300 may then record the safety information of the medication at 308. Then, method 300 may continue to FIG. 3B, specifically to 326 of method 300.

Returning to 304 of method 300, if it is determined that the literature is not a regulatory report, method 300 may proceed to 310 and determine if the study relates to a particular medical condition. The medical condition may be a medical condition input by the user via the user device. Thus, the method at 300 may determine if a particular piece of scientific literature (e.g., clinical study, FDA approved study, etc.) relates to a search of a specific medical condition by a user. As an example, if a user inputs high cholesterol as a medical condition, the method 300 may determine at 310, if a piece of scientific literature relates to a study involving reducing high cholesterol levels. If the literature does not relate to the medical condition at 310, then the method returns. However, if the literature does relate to the medical condition at 310, the method 300 may continue to 312.

At 312, the method 300 may comprise determining if the study relates to a user profile such as the user profile described above with reference to FIG. 2B. The user profile may include information such as the age, gender, ethnicity, medical history, etc., of a patient (user). Thus, the method 300 at 312 may include determining if a threshold number of patients in the study share one or more common characteristics with the user. In one example the threshold may be a threshold number of patients. In another example, the threshold may be a threshold percent of patients. As an example, it may be determined if the threshold percent of the patients in the study were of a similar age and gender to the current user. In other examples, the common shared characteristics between patients in the study and the user, used to determine if the study relates to the user may include shared medical histories, other medical conditions and medications used to treat those medical conditions, preferences, etc. If the study does not relate to the user profile, the method 300 then returns.

However if at 312, it is determined that the study does relate to the user profile, then method 300 may continue to 314 and determine if the study has a minimum number of participants. The minimum number of participants may be a fixed number of participants, below which the results of a study may be considered incomplete or invalid. In other words, the minimum number of participants may represent a threshold number of participants that may be sufficient to consider the results of a study significant. If the study does not have the minimum number of participants, then the method 300 may return. However, if the study does have at least the minimum number of participants, method 300 may continue to 316 and determine if the study meets clinical standards.

The clinical standards may include FDA approved studies, standards, and protocols. If the study does not meet the clinical standards at 316, method 300 may then return. However, if it is determined at 316 that the study meets the clinical standards at 316, then the method may continue to 318 and determine if the study outcomes have measurable results. Said another way, the method 300 at 318 may include determining if the study tested quantifiable variables. Thus a study outcome may have measurable results if the effects of a medication can be directly measured. As an example, a quantifiable variable may include blood pressure, heart rate, etc. In other examples, the method at 318 may additionally include determining if the medication in the study produced significant results in the patients of the study. Thus, the method at 318 may include determining if a particular medication helped treat a medical condition, or if it had little to no effect.

If it is determined that the study does not have measurable results, then method 300 may return. However, if it is determined at 318 that the study does have measurable results, then method 300 may continue to 320 and it may be determined if the scientific literature is a single clinical trial study. If the scientific literature is a single clinical trial, the method may continue to 323 and appraise the study using single clinical trial standards. The single clinical trial standards may be described in greater detail below with reference to FIG. 5. If it is determined at 320 that the literature is not a single clinical trial, then method 300 may continue to 324 and appraise the literature using a meta-study standard. The meta-analysis study standards may be described in greater detail below with reference to FIGS. 4A and 4B. Method 300 may then proceed from either 324 or 323 to 326 and record the study results. The method 300 at 326 may include storing the results of the study in a data-holding system (e.g., data-holding subsystem 204 from FIG. 2A). Method 300 may then continue to on to 328 in FIG. 3B. Method 300 may repeat multiple times, and as such may evaluate a plurality of scientific literature pertaining to single medication. Thus, after several iteration of method 300 for a given medication, the results of more than one study may be stored in the data-holding system.

Moving on to FIG. 3B, method 300 continues from 326 to 328 and calculates a weighted score for the study. The weighted score may be based on one or more of the effectiveness of the medication in treating the condition, the relative amount of similarity between the patients in the study and the current user, the confidence of the results of the study which may be based on the number of participants, etc. In one embodiment, the weighting may include assigning a higher weight to the study results from patients sharing similar characteristics with the current patient. Thus, with increasing similarity (e.g., number of shared characteristics) between a patient in the study and the current patient, the higher the results from that patient may be weighted relative to other patient results. The shared characteristics may include both medical and non-medical information as stored in the user profile. After determining the weighted score for the study at 328, method 300 may then update the medication score using the weighted study score at 330. The score assigned to a medication may be based on several studies already stored in the data-holding system. Thus at 330, the method may include updating the score assigned to a medication based on the weighted score of the current study. In another example, if at 330, method 300 has not evaluated any scientific literature for the particular medication/medication, then the weighted score may be used as the medication score at 330.

After using the weighted study score to update the medication score at 330, method 300 may continue to 332 and determine the effectiveness of the medication/medication using an aggregate score. The aggregate score may be based on the results from one or more studies stored in the data-holding system at 326. Thus, the aggregate score for a medication may be computed based on combining results from a plurality of studies. As such, the aggregate score may be indicative of the effectiveness of a medication in treating a particular medical condition.

After determining the effectiveness of the medication at 332, method 300 may continue to 334 and the certainty of the effectiveness may be determined. The certainty of the effectiveness may be based on the number of studies used to determine the effectiveness, the number of participants in those studies, proportion of participants in those studies that share a common characteristic with the user, number of shared characteristics with the user, etc. Said another way, the certainty of the effectiveness may increase with increasing numbers of studies, participants in those studies, validity of study methodology, thoroughness of reporting of study methodology details, and shared characteristics of patients in those studies with a user. The certainty may be a confidence interval, which may contain the actual effectiveness of the medication.

Method 300 may then proceed from either 334 or from 308 in FIG. 3A to 336 and the safety profile of the medication may be evaluated. The safety profile evaluation may include determining the side effects and health risks of taking the medication. Method 300 at 336 may additionally include determining the side effects and health risks of taking the medication specifically for the user. As an example, if a user is taking another medication that may cause a potential health risk when taken in combination with the current medication, then a safety concern may be recorded. Thus, the method 300 at 336 may include using the patient profile information to determine health risks to the user in taking the medication.

After determining the safety profile of the medication, a user personalized grade for the medication specific to the condition and user population may be assigned and/or modified. An example method for grading a medication is shown below with reference to FIG. 6. In one example, as shown in FIG. 6, the user personalized grade assigned to the medication may be a letter grade such as "A," "B," "C," etc. In another example the user personalized grade assigned to the medication be a number on scale such as "3 out of 5". In other examples the scale may be a different metric comprising symbols, or objects, such as "3 out of 5 stars." A user personalized grade may be assigned to the medication if there is no existing user personalized grade for the medication. If a user personalized grade has already been assigned to the medication at 338, then the user personalized grade may be modified to incorporate the newly evaluated study. The user personalized grade assigned to the medication may be based on the effectiveness determined at 332, the certainty of the effectiveness as determined at 334, the safety profile of the medication as determined at 336, the effectiveness of the medication amongst a subset of patients in the study sharing at least a threshold number of characteristics with the user, etc. Thus, the user personalized grade of a medication may match characteristics of the user to patients in the study sharing those characteristics. As such, results from those patients sharing more characteristics in common with the user may be weighted more heavily when calculating the user personalized grade for that medication. As an example, if the overall effectiveness of a medication in treating a particular condition is at a lower first level, but the effectiveness of that medication amongst a subset of the patients sharing at least a threshold number of common characteristic with the user is at a higher second level, the second level being higher and thus more effective than the first level, then the user personalized grade assigned to that medication may be increased. As described earlier, the shared characteristics between a patient in the study and the current patient/user may include both medical information and non-medical information such as lifestyle, preferences, hobbies, work conditions, etc.

Method 300 may therefore search available scientific literature to determine the effectiveness of that medication. Further, the effectiveness may be based on characteristics of the user. Specifically, depending on characteristics of a user such as age, gender, existing medical conditions and medications, etc., the predicted effectiveness of a medication may be adjusted. Thus, the predicted effectiveness of a medication may be increased if a large number of participants in studies involving that medication shared similar characteristics with the user such as similar age and/or gender. Therefore, the effectiveness of a medication may be based not only on the effectiveness of all patients in one or more studies, but may also be based on a subset of the patients in those studies sharing one or more characteristics with a user. Thus, for increases in the overall effectiveness of the medication, number of participants, number of studies, number of participants sharing characteristics with the user, number of shared characteristics with the user, the predicted effectiveness of the medication may increase. As a result the accuracy of the predicted effectiveness of a medication in treating a particular medical condition may be improved. Further, method 300 may involve incorporating other factors besides the effectiveness of the medication into the user personalized grade it receives. For example, health risks, side effects, and other safety factors may be used to determine the user personalized grade assigned to a medication.

With regards to FIGS. 4A and 4B, they show a method 400 for appraising an individual study using single clinical trial standards as described above at 323 with reference to method 300 in FIG. 3A. As such, method 400 may be executed at 323 of method 300 and may be included within method 300. Said another way, method 400 may be executed at 323 of method 300. Instructions for carrying out method 400 may be stored in the memory of a computer and/or server (e.g., data holding subsystem 204 of server 202 from FIG. 2A). As such, method 400 may be carried out by a logic system (e.g., logic subsystem 203 from FIG. 2A) of the computer and/or server.

Method 400 begins at 402 by reviewing study elements to determine a confidence interval for the study results. A confidence interval may be constructed based on the distribution of the results from the study, the standard deviation and mean of that distribution, etc. After determining the confidence interval at 402, method 400 proceeds to 404 and it is determined if the study is a retrospectively design trial. A retrospectively design trial may be a case-control study in which observations about two different groups of patients are used to draw conclusions about what may be causing differences between the groups. If it is determined that the study is a retrospectively design trial, then method 400 may proceed to 406 and the study may be assigned low confidence. Method 400 may then return. However, if the study is not a retrospectively design trial, then method 400 may continue to 408 and it may be determined if there are endpoint concerns. Specifically, the method at 408 may include determining if the results of the study could have happened by random chance, or if the confidence of the results is above a threshold to directly infer a correlation and/or causation between the medication and effects of the medication in the study. The endpoint concerns may comprise one or more of a correlate endpoint, subjective endpoint with lack of binding, inadequate binding. Additionally an endpoint concern may exist if an endpoint is defined post-hoc, and/or if it is an inappropriate measurement. If endpoint concerns exist, method 400 may continue to 406 and assign a low confidence to the study results. The method may then return.

If the endpoint concerns are unknown, the method 400 may proceed to 410 and record the endpoint concerns as a moderate concern. The endpoint concerns may be unknown if there are non-validated surrogate endpoints, and/or composite endpoints. Method 400 may then proceed to 412 from either 410, or from 408 if there are no endpoint concerns. At 412, the method 400 may include determining if there are study population concerns. The study population concerns may include a misrepresentative sample population and/or if the population is inappropriate to the endpoints. If there are study population concerns, then method 400 may continue to 406 and assign a low confidence to the study results. The method may then return.

If the study population concerns are unknown, method 400 may continue to 414 and record a moderate concern. The population concerns may be unknown if the population is poorly defined. Method 400 may then proceed to 416 from either 414, or from 412 if it is determined that there are no study population concerns. At 416, the method 400 may include determining if there are treatment concerns. Treatment concerns may include, patients taking other medication that could confound results, the dosage and frequency of administration of the medication, etc. Thus, in one example if the dosing is inadequate, or if the medication is taken for an insufficient duration, then it may be determined that a treatment concern exists. If there are treatment concerns at 416, then method 400 may continue to 406 and assign a low confidence to the study results. The method may then return. If treatment concerns are unknown at 416, then method 400 may proceed to 418 and record a moderate concern for the study results. Treatment concerns may be unknown due to an inappropriate comparator. Method 400 may then proceed to 420 from either 418, or from 416 if it is determined that there are no treatment concerns.

At 420, method 400 may include determining if the results can be generalized. Determining if the results can be generalized may include, determining based on the sample size and diversity of the sample size of the patients in the study, if the results of the study can be applied to a much larger population of patients. If it is determined that the results cannot be generalized at 420, then method 400 may proceed to 406 and assign a low confidence to the study results. The method may then return. If it is unknown whether the results can be generalized due to insufficient information then method 400 may proceed 422 and record a moderate concern for the study results. Method 400 may then continue from either 422 or from 420 if it is determined that the study results can be generalized to 424. At 424, the method 400 may include determining if there are safety and/or adverse events concerns. If it is determined that the population analyzed in the study for safety was incomplete or inappropriate, then it may be determined that there is a safety concern, and method 400 may continue to 406 and assign a low confidence to the study results. The method may then return. If the adverse events are not fully reported at 424, then method 400 may proceed to 426 and record the lack of reporting as a moderate concern.

Method 400 may then proceed to 428 from either 426 or from 424 if it is determined that there are no safety concerns. At 428, method 400 may include determining if there are intent to treat analysis concerns. Intent to treat analysis concerns may comprise failing to include a patient in data analysis regardless of that patient's adherence to a protocol and/or study completion once that patient had been randomized. Analysis concerns may include a proportion of patients who completed the study, a proportion of patient assigned in a group for the primary endpoint, difference between completion rates of different sample groups, etc. If it is determined that there is an analysis concern at 428, method 400 may proceed to 406 and assign a low confidence to the study results. The method may then return. An analysis concern may be identified if one or more of the following are satisfied: less than an upper first threshold proportion of patients completed the study, less than a threshold proportion of patients were assigned to the group for the primary endpoint, greater than a threshold difference in completion rates between two groups.

If it is determined that the proportion of patients who completed the study is greater than the lower first threshold but less than an upper second threshold, where the second threshold is greater than the first threshold, then method 400 may continue to 430 and record a moderate concern for the study results. Method 400 may then continue to 432 in FIG. 4B from either 430 in FIG. 4A, or from 428 if it is determined at 428 that there are no analysis concerns. It may be determined that there are no analysis concerns if the proportion of patients who completed the study is greater than the upper second threshold.

Continuing to FIG. 4B from FIG. 4A, method 400 may proceed to 432 and determine if there are sample and/or power size concerns with the study results. It may be determined if there are sample and/or power size concerns based on the confidence intervals of the study results, and the statistical significance of the study results. If the study results have insignificant differences, confidence intervals that are too large to draw any conclusion from the results, and/or confidence intervals are not provided, then it may be determined that there are sample and/or power size concerns. As such, method 400 may proceed to 406 and assign a low confidence to the study results. The method may then return.

If the sample and/or power size concerns are unknown due to lack of information, then method 400 may proceed to 434 and record a moderate safety concern for the study results. Method 400 may then continue to 436 from either 434, or from 432 if it is determined at 432 that there are no sample and/or power size concerns. At 436, method 400 may include determining if the study groups are randomized. If it is determined that the study groups are not randomized at 436, then method 400 may continue 406 and assign a low confidence to the study results. The method may then return. If it is unknown whether the study groups are randomized due to lack of information, method 400 may proceed to 438 and record a moderate concern for the study results. Method 400 may then continue to 440 from either 438, or from 436 if it is determined at 436 that the study groups were randomized. At 440, the method 400 may comprise determining if the study concealed allocation of the medication. Concealment of the allocation may include, blinding clinicians in the study to medication they are providing the patients in the study. If it is determined that the study did not practice effective concealment of allocation, then method 400 may proceed to 406 and assign a low confidence to the study results. The method may then return.

If it is unknown whether concealment of allocation took place in the study due to lack of information then method 400 may proceed to 442 and record a moderate safety concern for the study results. Method 400 may then continue to 442 from either 442, or from 440 if it is determined at 440 that there was proper concealment of allocation. At 444, method 400 may comprise determining if there was blinding in the study. Blinding may involve ensuring that the patients were unaware of the group they were assigned to. As an example, a blinded patient may be unaware if they are taking an actual medication or a placebo. If it is determined that the patients were not blinded in the study, and were aware of the group they were placed in, then method 400 may proceed to 406 and assign a low confidence to the results from the study. The method may then return.

If it is unknown whether the study properly blinded the patients due to lack of information, then method 400 may continue to 446 and record a moderate safety concern for the study results. Method 400 may then continue to 448 from either 446 or from 444 if it is determined at 444 that there was proper blinding of the patients. At 448, method 400 may comprise determining if concomitant medication confounded the study results. Thus, it if is determined at 448 that patients were taking medications outside of the study that could have affected the results of the study, then method 400 may proceed to 406 and assign a low confidence to the study results. The method may then return. If at 448, it is unknown if concomitant medication confounded study results due to lack of information, then method 400 may continue to 450 and record a moderate safety concern for the study results.

Method 400 may then continue to 452 from either 450 or from 448 if it is determined at 448 that the results were not confounded by concomitant medication. At 452 it may be determined if there are drug wash out concerns. Wash out concerns may include if a patient in the study stops taking a drug in such close proximity to the study that the effects of taking that medication confound the result of the study. Thus, a wash out concerns may include if a patient in the study was still taking medications within a threshold amount of time before the onset of the study. If it is determined that there are wash out period concerns at 452, method 400 may proceed to 406 and assign a low confidence to the study results. The method may then return.

If it is unknown if there are wash out concerns at 452 due to a lack of information, then method 400 may proceed to 454 and record a moderate concern for the study results. Method 400 may then continue to 456 from either 454 or from 452 if it is determined at 452 that there are no drug wash out period concerns. At 456 it is determined if there are statistic concerns. Statistic concerns may include any artifacts which may confound the study results such as clinician-statistician interaction and communication, faulty reporting, inferring causation in place of association, multiplicity of hypothesis, missing data, etc. If it is determined that there are statistic concerns and that they are identified post-hoc, after the analysis of the study results, then method 400 may proceed to 406 and assign a low confidence to the study results. The method may then return. If one or more statistical concerns exist, but they were pre-identified before analysis of the study results, then method 400 may continue to 458 and record a moderate concern for the study results. Method 400 may then continue to 460 from either 458 or from 456 if it is determined at 456 that there are no statistic concerns. At 460, the method 400 may comprise determining if there are more than two total moderate concerns recorded. Thus, if method 400 recorded a modern concern at least twice between 408 and 460, then method 400 may continue to 462, and determine if the moderate concerns make the study unreliable. If it is determined at 462 that the two or more moderate concerns make the study unreliable, then method 400 may proceed to 406 and assign a low confidence to the study results. The method may then return.

However, if at 462 the two or more moderate concerns do not make the study unreliable, then method 400 may continue to 466 and assign a moderate confidence to the study results. The method may then return. Returning to 460, if it is determined that there are less than two total moderate concerns for the study, then method 400 may proceed to 464 and determine if the study has any moderate concerns. If the study has one moderate concern, the method 400 continues to 466 and a moderate confidence is assigned to the study results. The method may then return. However, if no moderate concerns were assigned to the study, then method 400 may proceed from 464 to 468 and assign a high confidence to the study results. The method may then return.

Thus, the method 400 may comprise assessing the accuracy and/or confidence of results from an individual clinical study. The method 400 may include assessing whether a variety of clinical procedures and protocols were followed to reduce the chance of confounding results, and also assesses the accuracy of the statistical analysis used to evaluate the results from the study.

Turning now to FIG. 5, it shows a method 500 for appraising a meta-analysis study or systematic review. Specifically, method 500 may include appraising a study using meta-analysis standards as described above at 324 with reference to method 300 in FIG. 3A. As such, method 500 may be executed at 324 of method 300 and may be included within method 300. Said another way, method 500 may be executed at 324 of method 300. Instructions for carrying out method 500 may be stored in the memory of a computer and/or server (e.g., data holding subsystem 204 of server 202 from FIG. 2A). As such, method 500 may be carried out by a logic system (e.g., logic subsystem 203 from FIG. 2A) of the computer and/or server.

Method 500 may begin at 502 by reviewing the meta-study. After reviewing the meta-study at 502, the method 500 may proceed to 504 and determine if the study inclusion criteria is clearly defined. The study inclusion criteria may include criteria used to determine if a patient is eligible for participation in the study. If the study inclusion criteria is not clearly defined then method 500 may proceed to 506 and may assign a low confidence to the results of the meta-analysis study. The method may then return. However if it is determined at 504 that the study inclusion criteria is clearly defined in the meta-analysis study, then method 500 may continue to 508 and determine if the individual studies are critically appraised. In one example, critical appraisal may include a peer review process of the individual studies that attempts to detect sources of bias in the studies. If one or more of the studies have not been critically appraised, then method 500 may proceed to 506 and assign a low confidence to the meta-study results. Method 500 may then return.

However, if at 508 it is determined that the individual studies in the meta-study have all been critically appraised, then method 500 continues to 510 and determines if the results from the meta-study conclude that the treatment effect can be quantified. Thus, the method at 510 may comprise determining if the administration of the medication in the meta-study produced measurable, and significant effects in the patients of the study. If the treatment effect is not quantifiable, then method 500 may proceed from 510 to 506 and assign a low confidence to the meta-study results. Method 500 may then return. If at 510, it is determined that the treatment effect can be quantified, then method 500 may proceed to 512 and determine if there are any moderate concerns in the manner described above with reference to method 400 of FIGS. 4A and 4B. The moderate concerns include concerns with the confidence of the study results due to a lack of proper documentation and recording of the procedures, data analysis, protocols, etc., performed in the meta-study. As an example, some moderate concerns may include lack of provided information regarding the patient population, blinding of the patients, randomization of patients into study groups, etc. Other examples of moderate concerns are provided with reference above to method 400 in FIGS. 4A and 4B. If one or more moderate concerns are detected at 512, method 500 may proceed to 514 and assign a moderate confidence to the study results. Method 500 may then return. However, if at 512 it is determined that there are no moderate concerns with the study results, then method 500 may continue to 516 and assign a high confidence to the study results. Method 500 may then return.

Continuing to FIG. 6, an example method for assigning a letter grade to a medication based on the user personalized grade is shown. The letter grades in decreasing effectiveness are "A," "B," "C," "D," and "F." Thus, a medication assigned a letter grade of "A" may have a higher predicted effectiveness than a medication assigned a letter grade of "B," which may have a higher predicted effectiveness than a medication assigned a letter grade of "C," and so on. A letter grade of "PI" may signify that the medication is effective but has unknown risks. Thus, the effectiveness of a medication given a letter grade of "PI" may be approximately the same or similar to a medication for which the risks are known and assigned a letter grade of one or more of "A," "B," or "C." However, a letter grade of "I" may signify that the medication is not effective and may also have unknown risks. Thus, the effectiveness of a medication given a letter grade of "PI" may be approximately the same or similar to a medication for which the risks are known and assigned a letter grade of one or more of "D" and "F."

Specifically, method 600 shown in FIG. 6 may include appraising and assigning a user personalized grade to a medication based on results from one or more studies involving the medication and its treatment effects. In the example shown in method 600, the user personalized grade is a letter grade. However, it is important to note that in other embodiments, the user personalized grade may be represented on another grading scale such as via numbers, stars (e.g., 3 out of 5), checkmarks, or other visual comparison scales. Method 600 shows an example of grading a medication as described with reference to 338 of method 300 in FIG. 3B. As such, in one embodiment, the method 300 at 338 may include executing method 600. Said another way, method 600 may be executed at 338 of method 300. Thus, method 600 may comprise evaluating several collected studies concerning a particular medication, to determine a user personalized grade for the medication based on its effectiveness, risks, and safety concerns. Instructions for carrying out method 600 may be stored in the memory of a computer and/or server (e.g., data holding subsystem 204 of server 202 from FIG. 2A). As such, method 600 may be carried out by a logic system (e.g., logic subsystem 203 from FIG. 2A) of the computer and/or server.

Method 600 begins at 602 by determining if there is at least one high confidence study relating to a particular medication. A high confidence study may include either an individual study assigned a high confidence as is shown above with reference to 468 of method 400 in FIG. 4B, or a meta-study assigned a high confidence as is shown above with reference to 516 of method 500 in FIG. 5. If it is determined that there are no studies relating to the medication that have been assigned a high confidence, then method 600 proceeds to 604 and determines if there are two or more studies of fair (e.g., moderate) confidence. If there are no studies of high confidence and less than two studies of moderate confidence, then method 600 may proceed to 636 and determine if the safety risk of the medication decreases the net benefit of taking the medication. If the safety risk decreases the net benefit of taking the medication, the method 600 may assign the medication with a letter grade of "PI" at 640. If at 636, it is determined that the safety risk of taking the medication decreases the net benefit of the medication, or if it is unknown whether the safety risk decreases the net benefit of taking the medication, then method 600 may proceed to 638 and assign a letter grade of "I" to the medication. Method 600 may then return.

Returning to 604, if there are two or more studies of moderate confidence regarding the medication, then method 600 may proceed to 608 and determine if the magnitude of the benefit in the results and endpoints from the studies are clinically meaningful. If the results from the studies are not clinically meaningful, then method 600 may proceed to 636 and determine if the safety risk decreases the net benefit of taking the medication. Method 600 may then proceed to either 640 or 638 as described above. Returning to 608, if the magnitude of the benefit in the results and endpoint are clinically meaningful for the two or more studies of moderate confidence, then method 600 may proceed 610.

Returning to 602, if it is determined that at least one study for the medication has a high confidence level in its results, then method 600 may continue to 606. At 606, the method 600 may comprise determining if all of the study endpoints have a consistent magnitude of benefit. That is, at 606, the method may include determining if the studies have relatively consistent results. If the study endpoints do not have consistent magnitude of benefits, then method 600 may proceed to 636, which may involve determining if the safety risk associated with the medication decreases the net benefit of taking the medication. Method 600 may then proceed to either 640 or 638 as described above. However, if at 606 it is determined that the study endpoints do have consistent magnitude of benefits, then method 600 may continue to 610. Therefore method 600 may continue to 610 from either 608 or 606.

At 610, the method 600 comprises determining if the medication is more effective than no treatment. If it is determined at 610 that taking the medication would be no more effective in treating a medical condition than not taking medication, method 600 may continue to 628 and determine if the safety risk associated with the medication decreases the net benefit of taking the medication. If the safety risk does not decrease the net benefit of taking the medication, then method 600 may continue from 628 to 630 and assign a letter grade of "C" to the medication. Method 600 may then return. However, it at 628 it is determined that the safety risk of taking the medication decreases any net benefit derived from taking the medication, then method 600 may proceed to 634 and assign a letter grade of "D" to the medication. Method 600 may then return. If it is unknown whether the safety risk of taking the medication decreases the net benefit of taking the medication then method 600 may proceed from 628 to 632 and assign a letter grade of "I" to the medication. Method 600 may then return.

Returning to 610, if it is determined that taking the medication is more effective in treating the medical condition than not taking the medication, then method 600 may continue to 612 and determine if the safety risks associated with taking the medication are known. If the safety risks are unknown, then method 600 may proceed to 626 and assign a letter grade of "PI" to the medication. Method 600 may then return.

However, if at 612 the safety risks associated with the medication are known, method 600 may continue to 614 and determine the extent of the net benefit provided to a patient taking the medication. If the net benefit of taking the medication is above a first threshold, then method 600 may continue to 616 and determine if the safety risk of taking the medication decreases the net benefit of taking the medication. If the safety risks of taking the medication decrease the net benefits derived from taking the medication, then method 600 may continue from 616 to 622 and assign a letter grade of "B" to the medication. Method 600 may then return. If however the safety risks associated with the medication are determined to not decrease the net benefits gained from taking the medication at 616, then method 600 may continue to 624 and assign a letter grade of "A" to the medication. Method 600 may then return.

Returning to 614, if the net benefit gained from taking the medication is below the threshold, then method 600 may proceed to 618 and determine if the safety risks associated with taking the medication decrease the net benefits gained from taking the medication. If the safety risks associated with the medication do not decrease the net benefit derived from taking the medication, then method 600 may proceed from 618 to 622 and assign a letter grade of "B" to the medication. Method 600 may then return. However, it at 618 it is determined that the safety risks associated with the medication decrease the net benefit derived from taking the medication, then method 600 continues to 620 and may assign a letter grade of "C" to the medication.

The method 600 involves assigning a letter grade to a medication based on the effectiveness of the medication and the potential health risks associated with taking the medication. Further, the letter grade assigned to a medication is indicative of the user personalized grade calculated for the medication, which may be based on the number of studies using the medication, the confidence of the results of those studies, the effectiveness of the medication in treating a medical condition, and the safety risks associated with the medication that may decrease the net benefit of taking the medication. Thus, increases in the user personalized grade calculated and assigned to a medication may indicate an increase in the effectiveness of that medication, and/or a decrease in the safety concerns associated with that medication. The letter grades assigned to a medication in decreasing order of user personalized grade may include: "A," "B," "C," "D," "PI," and "I."

Thus, FIGS. 3-6 show example methods that may be performed in response to a user request for information regarding available medication options to treat a medical condition. Specifically, a server (e.g., server 202 from FIG. 2A) in communication with one or more remote servers (e.g., remote server 232) may retrieve information from databases (e.g., databases 233) stored in the one or more remote servers pertaining to the medications used in treating the medical condition of the user. The information retrieved from the remote server may include scientific literature, clinical studies, peer reviewed literature, information provided from the FDA, etc. A logic subsystem (e.g., logic subsystem 203 from FIG. 2A) may then execute various instructions, such as those previously described with reference to the methods included in FIGS. 3-6) to determine the efficacy, safety, and risks associated with one or more of the medications. Further, additional information regarding the medications may be obtained and/or analyzed including the cost, patient reviews, doctor recommendation, etc. After obtaining and/or analyzing information about various medications, that information may then be displayed to the user via the user interface. An example method for displaying various medication options available to a user with a particular medical condition is shown in FIG. 7.

Figure 7:
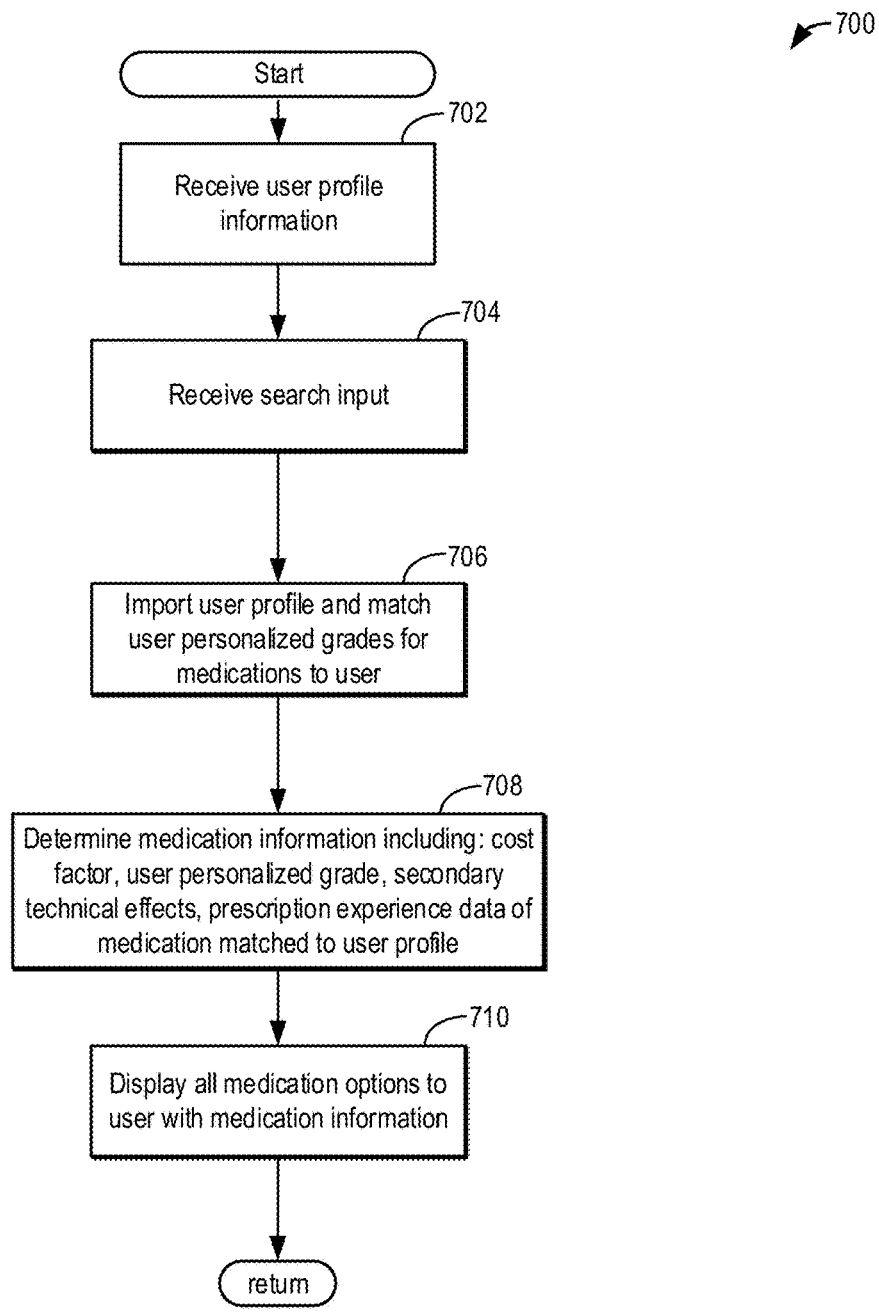
FIG. 7 shows a flow chart of a method for displaying various medication options to a user.

Turning now to FIG. 7, it shows a method 700 for displaying medication information to a user about one or more medications used in treating a particular medical condition. Such information may include information regarding the cost, effectiveness, user personalized grade, risks, safety, care provider recommendations, secondary technical effects, prescription experience data etc., of each medication. Instructions for carrying out method 700 may be stored in the memory of a computer and/or server (e.g., data holding subsystem 204 of server 202 from FIG. 2A). As such, method 700 may be carried out by a logic system (e.g., logic subsystem 203 from FIG. 2A) of the computer and/or server.

Method 700 begins at 702 which comprises receiving user profile information. As described above with reference to FIG. 3A, user profile information may include one or more of the age, gender, ethnicity, medical history, etc., of a user. Thus, user profile information may include both medical and non-medical information. After receiving user profile information the method may continue to 704. The method at 704 may comprise receiving search input from a user. In one embodiment, the search input at 704 may include a search request from the user for all medications relating to a medical condition. Thus, a user may input a search of a particular medical condition in order to see available medications used in treating said input medical condition. As an example, a user may input a search for high cholesterol, and request for feedback on medication used to treat high cholesterol. In another embodiment the user may search by medication at 704. Thus, a user may input a specific medication, and request information about that particular medication. As an example, a user may search "Lovastatin," for information about that medication, and for what medical conditions it may be used.

After receiving search input at 704, method 700 may then continue to 706 and import the user profile and match treatment user personalized grades to the user. Specifically, the method 700 at 706 may comprise, based on the input received at 704, querying one or more medication databases (e.g., databases 233 described above with reference to FIG. 2) for information relating to medications associated with the search input at 704, and querying a patient profile database (e.g., database 234 described above with reference to FIG. 2) for patient information. Further, the method 700 at 706, may comprise retrieving the medication information from the one or more medication databases and retrieving the patient profile information from the patient profile database. As described in greater detail above with reference to FIG. 3, based on information about the user stored in the user profile, a unique user personalized grade may be assigned to each available medication. Thus, the effectiveness, safety, health risks, all of which may be used in determining the user personalized grade of a medication, may change depending on the information provided by the user in their user profile. As an example, a medication whose side effects may include seizures, may be assigned a lower user personalized grade to a user who has epilepsy, than a patient who does not have epilepsy.

Thus, the calculating the user personalized grade may be based on one or more of the clinical effectiveness of the medications, prescription experience data, cost factor, insurance coverage, care provider recommendations, and technical secondary effects. Further, in some examples, one or more of the clinical effectiveness of the medications, prescription experience data, cost factor, insurance coverage, care provider recommendations, and technical secondary effects may be differentially weighted when calculating the user personalized grade. As one example, the clinical effectiveness may be weighted more heavily than the prescription experience data, cost factor, insurance coverage, care provider recommendations, and technical secondary effects. Thus the clinical effectiveness of the medication may have a larger influence on the user personalized grade the medication is assigned than the prescription experience data, cost factor, insurance coverage, care provider recommendations, and technical secondary effects.

Once, the medication user personalized grades have been correlated to the user profile, method 700 may then proceed to 708 and determine the cost factor, prescription experience data, secondary technical effects, etc., of the one or more medications matched to the user profile. As described earlier, the prescription experience data may include feedback, reviews, and comments from patients with experience with the medication. Secondary technical effects may be side effects of the medication as established in scientific literature and clinical testing of the medication. The cost factor may be indicative of the out-of-pocket cost of the medication to the user.

Then, after determining one or more of the cost factor, prescription experience data, secondary technical effects, etc., of the one or more medication matched to the user profile, the method 700 may continue to 710. At 710, the method 700 may include displaying all medication options to the user with relevant information about the medication. The medication may be displayed via a display screen (e.g., display subsystem 225 from FIG. 2A) to a user on a user device (e.g., user device 222 from FIG. 2A). The relevant information about the medication may include the cost factor, prescription experience data, secondary technical effects, safety, health risks, effectiveness, and care provider recommendations, of the medication. In other examples the relevant information may include direct electronic connections to one or more scientific research articles used in determining the effectiveness and/or user personalized grade of the medication. It is important to note that the medications may include medications produced by more than one pharmaceutical company. Method 700 may then return.

Various example displays which may be presented to a user regarding medication options are shown below in FIGS. 8A-8G. Thus, FIGS. 8A-8G may show example interfaces displayed to a user on a display system (e.g., display subsystem 225 from FIG. 2A), to allow a user to compare medications. Further, FIGS. 8A-8G show an example user interface through which a user may interact with a healthcare platform (e.g., healthcare platform 100).

Figure 8A:
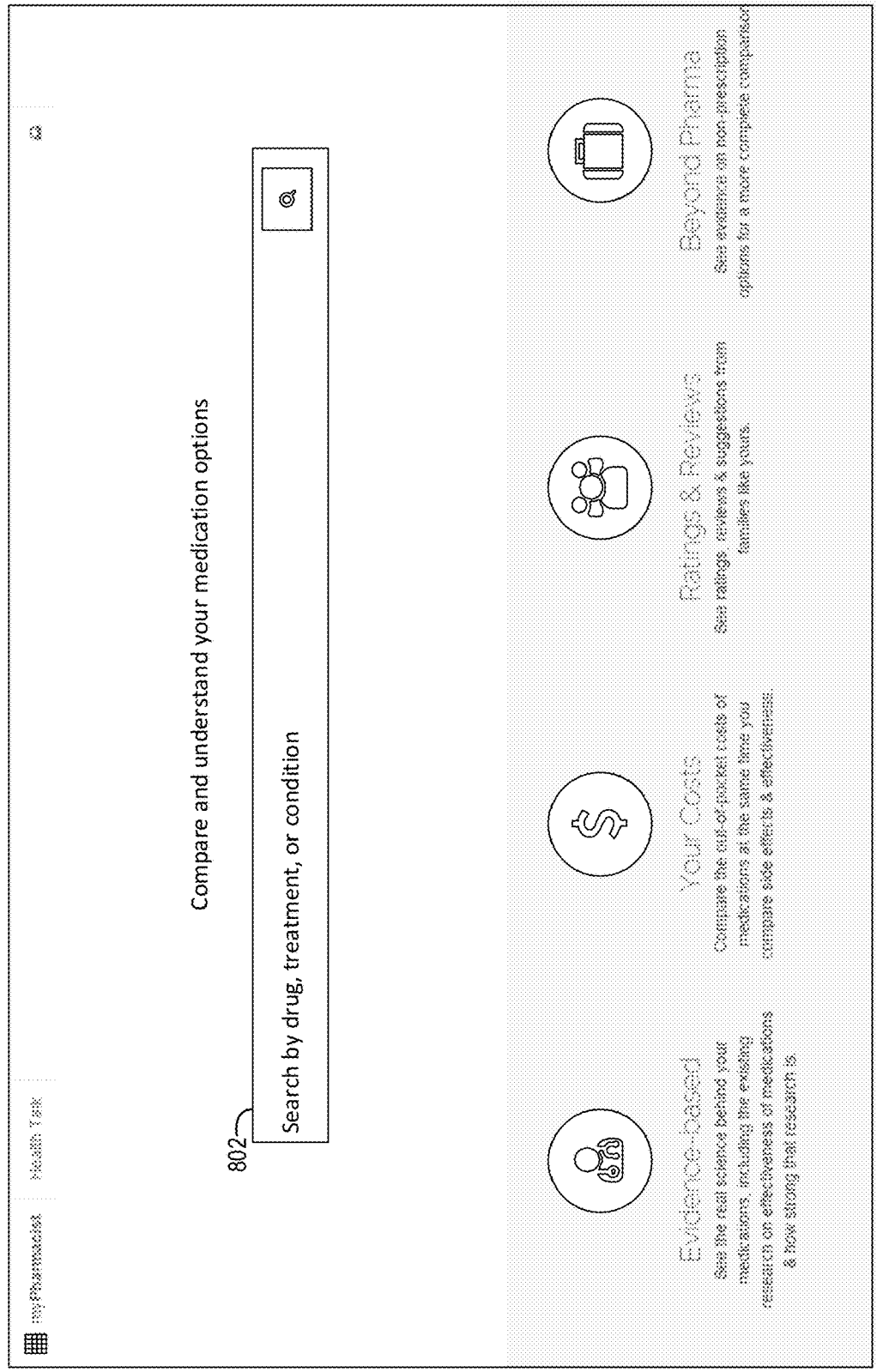
FIG. 8A illustrates an example online health care platform interface for a user.
Figure 8B:
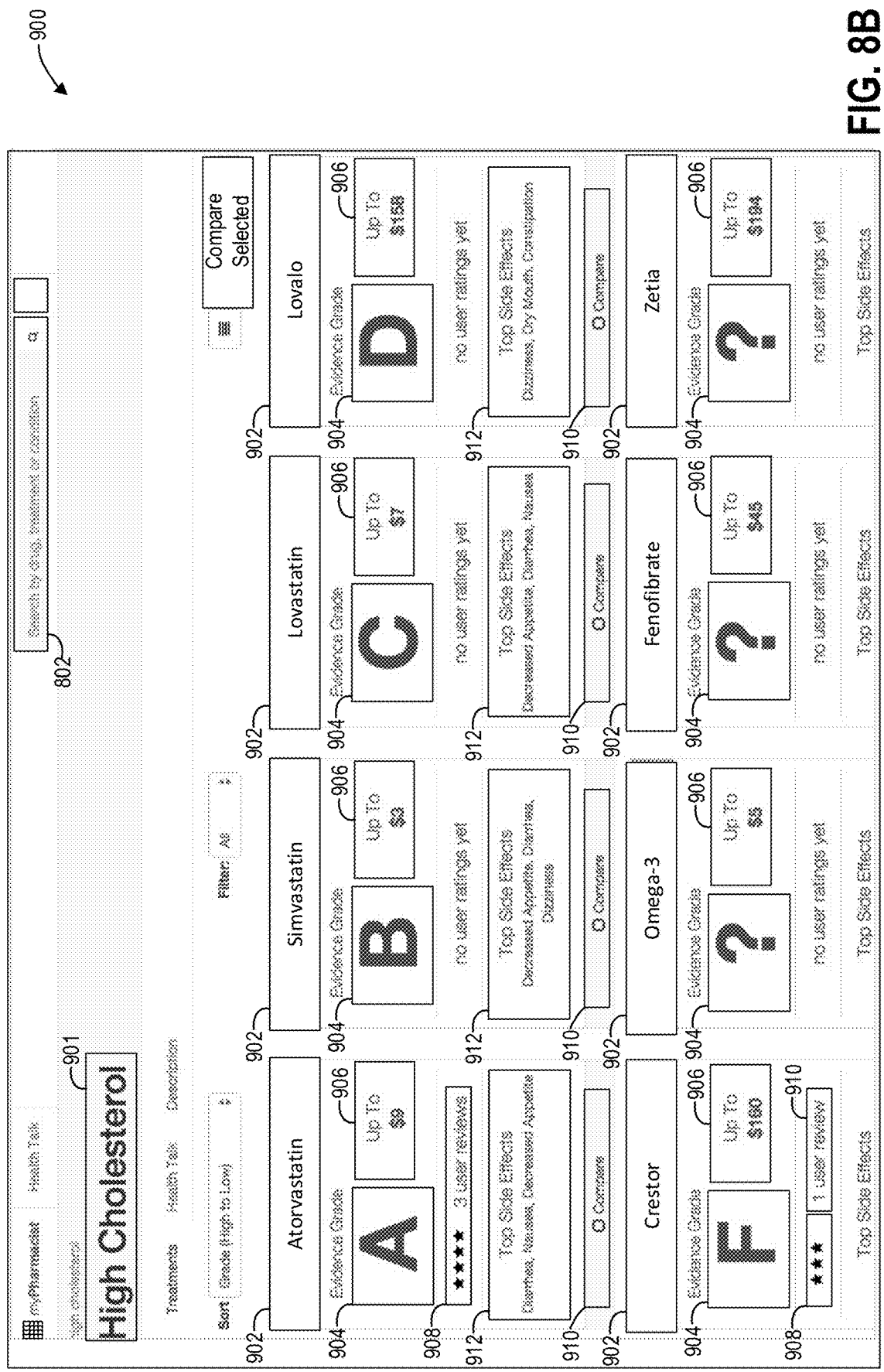
FIG. 8B illustrates an example online health care platform interface for a user.

Turning to FIG. 8A, it shows a first display 800, which may resemble a search engine, and may prompt a user to search for medications. As such the display 800 may include a search field 802, which allows a user to type in a search. In one example a user may search for a specific medication. As an example, a user may input "Lovastatin." In other examples the user input a medical condition and search for available medication used to treat said medical condition. As an example, a user may input "high cholesterol." The display 800 may additional include an icon identifying the user. In one example the icon may be a picture of the user. As such, the icon may be used to represent the user currently signed in to the healthcare platform. By looking at the icon, a user may be able to identify it they are the one signed into the healthcare platform. Next to the icon, there may be an option for a user to select to "sign out" of the current user profile, if it does not match their user profile.

Turning now to FIG. 8B, it shows a second display 900, which may presented to the user after the user has input a search element 901 into the search field 802, such as a medication, or medical condition. Specifically, second display 900 shows a display that may be presented to a user if the search element 901 input by the user in the search field 802 is "high cholesterol." As shown in FIG. 8B, the search element 901, may be presented to the user on the second display 900. Thus, second display 900, may show a search report which would be presented to a user in response to a search for high cholesterol. Several medications used in treating the medical condition may be presented side-by-side to one another. The medication names 902, their cost factor 906, user personalized grade 904, secondary technical effects 912, user reviews, and a link to scientific articles mentioning the medication may all be provided on the same display 900. A user may sort the medication by the cost 906 and/or user personalized grade 904 of the medication. As shown in the example provided in FIG. 8B, the medications are sorted by user personalized grade 904 from highest to lowest user personalized grade 904. A user may also apply various filters such as to only include certain medications depending on the preference of the user. For example a user may filter medications so that only medications that have been FDA approved may be displayed on the display 900.

In the example shown in second display 900, several high cholesterol medications may be presented such as Atorvastatin, Simvastatin, Lovastatin, and Livalo. Along with the name 902 of the medication, a user personalized grade 904 for each medication may also be provided directly below the name 902 of the medication. In the example shown, the user personalized grade 904 may be a letter grade such as "A," "B," "C," "D," or "F," where the letter grade may indicate the predicted effectiveness of the medication. In other example, the letter grade may also be based on one or more of the predicted safety, health risks, costs, care provider recommendations, etc., of the medications. The letter grade may be obtained by evaluating scientific research conducted on the medication, for example in the manner described above with reference FIGS. 3-7. If there is not enough available published information regarding the effectiveness of the medication, then the medication may not be assigned a user personalized grade.

In addition to the user personalized grade 904, the cost factor 906 of the medication may also be displayed directly below the name of each medication, and next to the user personalized grade 904. The cost factor 906 may include both the cost of the medication before and after the deductible. Additionally, the cost factor 906 may be based on a user's insurance plan, benefits, coinsurance, copay, etc. Below the name 902 of each medication, the display 900 may additionally include a user review bar 908. The user review bar 908 may include an average user score of the medication. In the example shown in FIG. 8B, the user review bar 908 may be an average user review out of five stars. Thus, users who have taken the medication can assign a score to the medication anywhere from zero to five stars. Additionally, the secondary technical effects 912 for the medications may also be presented. In one example the secondary technical effects 912 may be presented directly below the user review bar 908. Further, and not shown in FIG. 8B, the second display 900 may also include an icon which the user can select to take the user to the scientific articles used in formulating the user personalized grade of the medication. Thus, the user can click on the icon and be re-directed to the one or more scientific articles that were used in determining the user personalized grade assigned to the medication. As such, display 900 allows users easy access to peer-reviewed literature which details the effectiveness, safety, etc. of a medication in clinical studies with patients similar to the current user.

Display 900 may also include a compare icon 910 which a user may select to compare specific medications from the initial list of medications provided in the display 900. For example, a user may select the compare icon 910 from two or more medications listed in the second display 900, and compare those two or more medication based on additional parameters not included in the second display 900. An example display is shown in FIG. 8C that may be presented to a user in response to the user selecting the compare icon 910 for two or more medications.

Figure 8C:
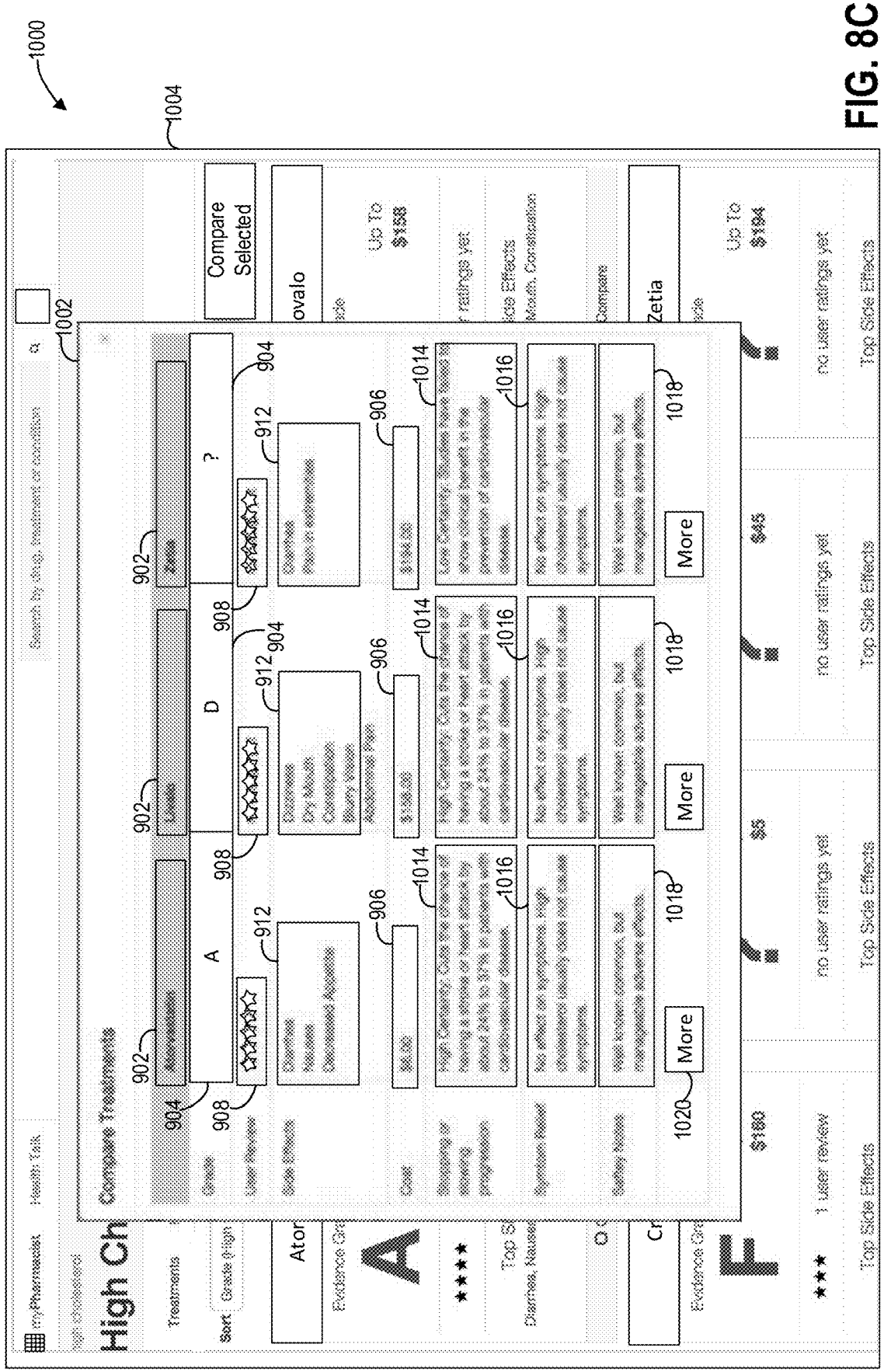
FIG. 8C illustrates an example online health care platform interface for a user.
Figure 8D:
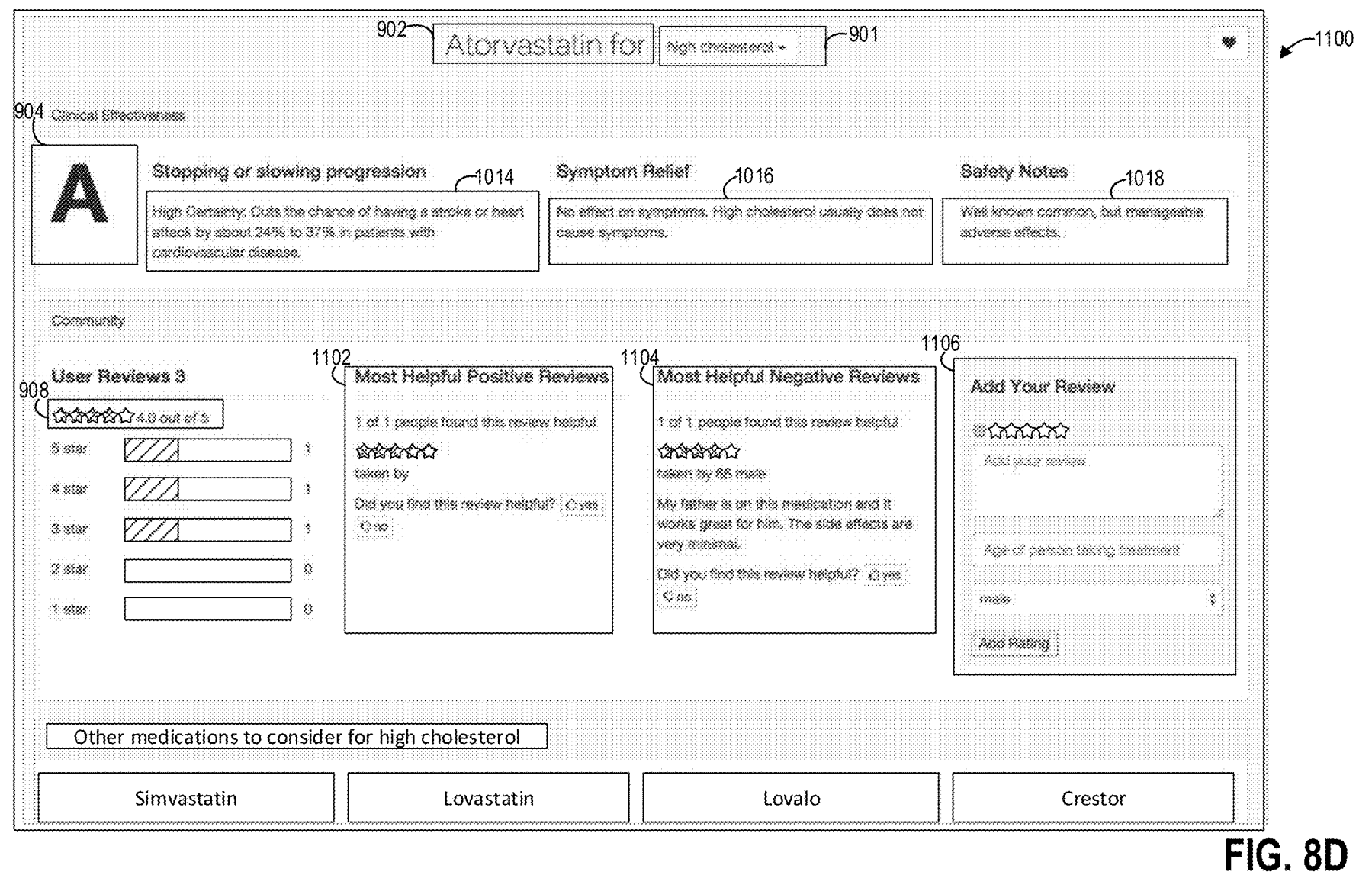
Figure 8E:
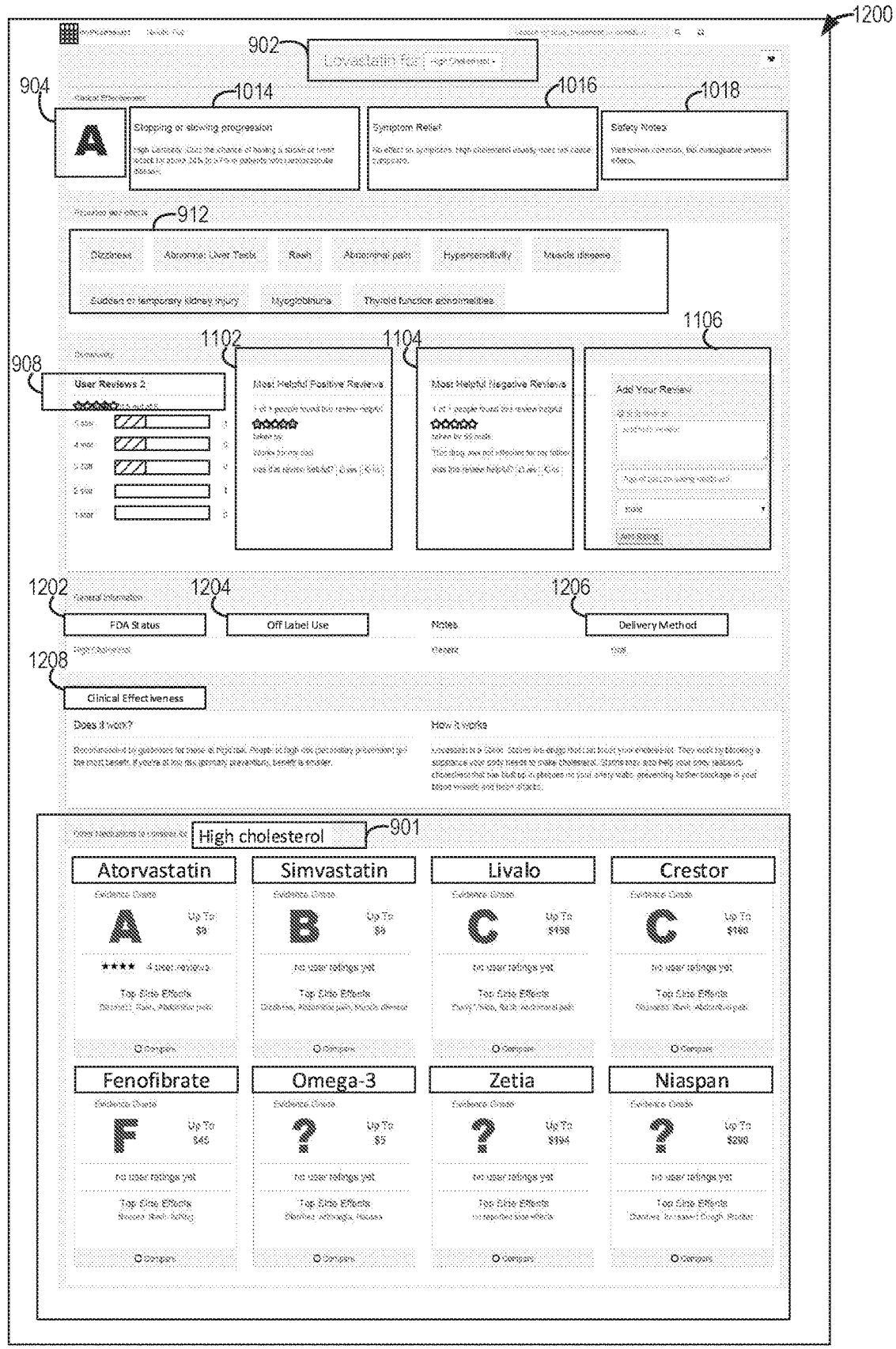
FIG. 8E illustrates an example online health care platform interface for a user.
Figure 8F:
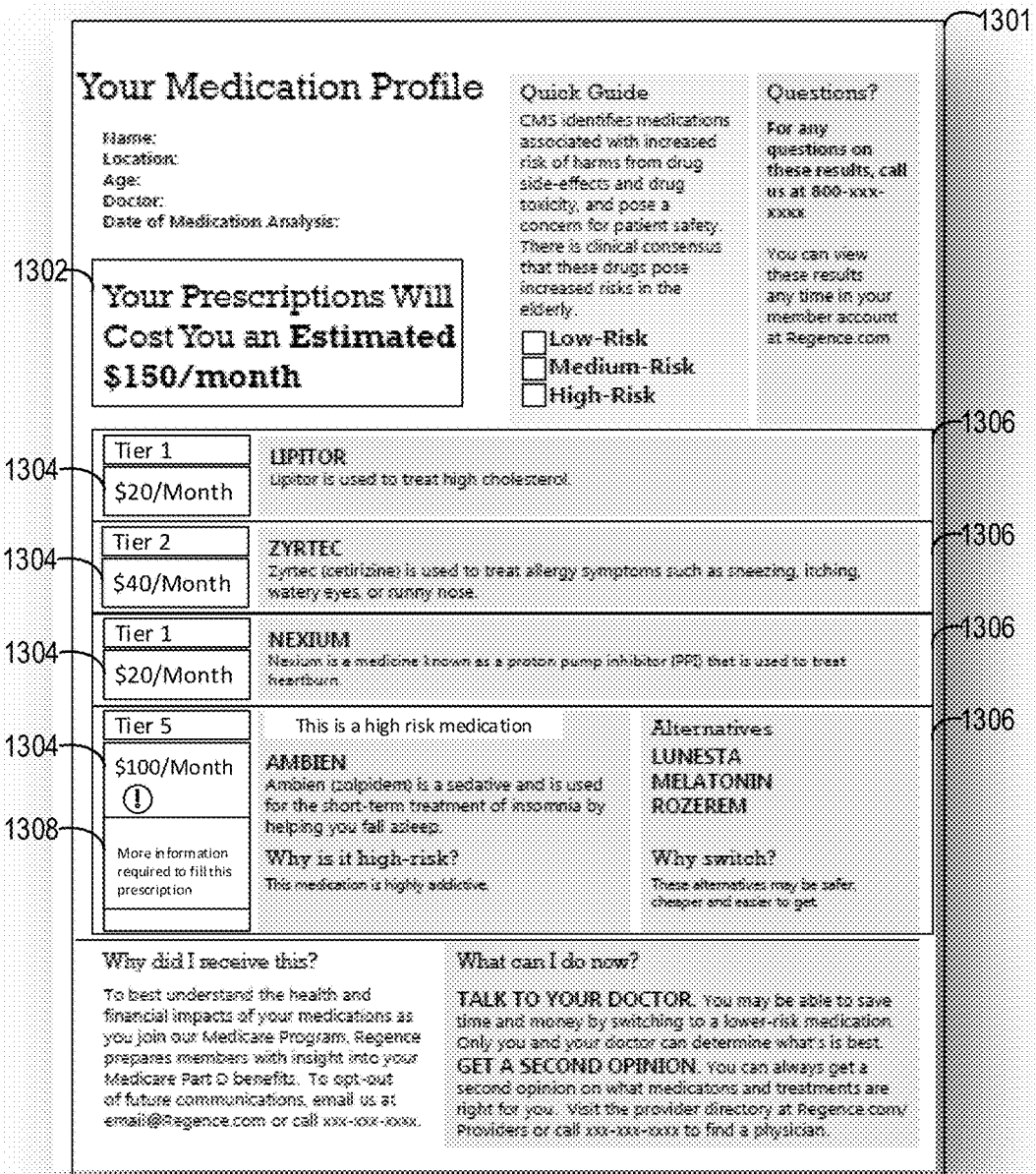
FIG. 8F illustrates an example online health care platform interface for a user.

Turning now to FIG. 8C, it shows a third display 1000, that is an example of a display that may be presented to a user after a user selects to compare two or more medications from an initial medication list, for example in the manner described above in FIG. 8B. The two or more medications selected by the user for comparison may be presented in a first screen 1002 overlaid on a second screen which 1004 where the second screen 1004 may be the same or similar to display 900 described above with reference to FIG. 8B. Thus, information regarding the medication the user wishes to compare may be presented on top of the display of the list of medication provided in display 900. As such, the first screen 1002 may only cover a portion of the second screen 1004, allowing the user to still see a portion of the list of medication included in the second screen 1004. The first screen 1002 may compare the medications and information about the medication side by side to one another. In the example shown in FIG. 8C, the name 902 of each medication may be arranged in vertical columns, and medication information about each medication may be presented in horizontal rows.

The medication information about the medications, may include the user personalized grade 904, secondary technical effects 912, cost factor 906, prescription experience data or user review bar 908, side effects, and cost, similar to the information provided in FIG. 8B. However, the screen 1002 may additionally include a symptom relief tab 1016 including information on whether or not the medication relieves symptoms associated with the medical condition, a prognosis tab 1014 including information about whether the medication stops and/or slow the progression of the medical condition, and a safety notes tab 1018 including safety information about the medication. An icon 1020 below each medication may also be provided which may allow a user to select and acquire additional information about each specific medication. An example display screen that may be presented to a user, in response to a user selecting the icon 1020 to request more information about a medication is shown in FIG. 8D.

Turning now to FIG. 8D, a fourth display 1100, shows an example display that may be presented to a user, upon a user request for information about a specific medication. In the example shown in FIG. 8D, specific information about the medication Atorvastatin is shown. Thus, fourth display 1100 may only provide information about one medication, which the user may select for in third display 1000 via the icon 1020.

The information provided in fourth display 1100 may include the user personalized grade 904 of the medication, cost factor 906 user review tab 908, symptom relief tab 1016, safety notes tab 1018, and prognosis tab 1014. All of the above information about the medication may be included in the second display 900 and third display 1000. However, in addition to previously available information about the medication, fourth display 1100 may include user comments for the medication. Specifically the comments may be sorted in the positive review comments 1102 and negative review comments 1104 based on the score each user assigned to the medication. Additionally, fourth display 1100 may include a rating tab 1106 which allows the current user to add a medication review, which may include one or more of a score, comment, and personal information. Additionally, care provider recommendations regarding the medication may be provided in fourth display 1100. Further, a user may select an icon (not shown) which may direct the user to scientific literature mentioning the medication in one or more clinical studies.

As seen in FIG. 8D, below the information regarding the current medication (e.g., Atorvastatin), several other icons may be presented, which if selected, may direct a user to other individual medication options. The other medications options may include medications used in treating the same underlying medical condition of the current medication presented in FIG. 8D. Further, the other medications may include the same, or at least one or more of the medication presented to the user in the second display 900.

Moving on to FIG. 8E, it shows another example display 1200 which may be presented to a user. The display 1200 may be displayed to a user in response to the user searching for a specific medication in the search field at display 800. In the example, provided in FIG. 8E, the display 1200 may be presented to the user in response to the user searching for Lovastatin in the search field of display 800. In another embodiment, display 1200 may be presented to a user in response to the user selecting a specific medication from a list of medications provided to user in response to a search for a specific condition at display 800. As an example, display 1200 may be presented to the user in response to the user selecting Lovastatin from either display 900 from FIG. 8B, or from display 1000 in FIG. 8C.

Display 1200 may include information about a specific medication, in the example of FIG. 8E, Lovastatin. Information about the medication may include: a list of secondary technical effects, whether it relieves symptoms associated with the medical condition, whether it stops or slows progression of the medical condition, safety notes, user reviews, and user comments. Additionally, display 1200 may include general information about the medication such as an FDA status tab 1202 including information about whether or not the medication is FDA approved, an off label use tab 1204 including information about any reported off label uses of the medication, delivery method tab 1206 including information about how the medication is taken (e.g., pills taken orally, injections, liquid, etc.). The display 1200 may also allow a user to select a clinical effectiveness tab 1208 which when selected may direct the user to one or more of clinical studies, peer reviewed literature articles, and scientific literature articles that present results for the medication's tested effectiveness. Further, display 1200 may include information about what groups of patients benefited the most from taking the medication. For example, the medication may be more beneficial for a specific age range, gender, medical history and condition of a patient, etc. In the example shown in display 1200, Lovastatin may be most effective for patients who are at a high risk for high cholesterol and heart attack. Display 1200 may also include information on how the medication works. This may include the biological mechanisms under which the medication operates to treat the medical condition.

As shown in FIG. 8E, display 1200 may additionally include a list of other medications used in treating the same underlying medical condition. In the example shown in FIG. 8E, the list of alternative medication may be presented directly below the current medication information. The alternative medications may be presented to the user in a manner similar to that shown in display 900 of FIG. 8B, with a side by side comparison of the medications. Under each medication, medication information such as the cost, user personalized grade, user reviews, and side effects may also be presented for each medication.

Moving on to FIG. 8F, it may include a display 1300, that may show the medication profile of a user (e.g., patient profile from FIGS. 3A and 7). The display 1300 may include basic personal information about the user such as their name, location, age, gender, care provider, medical doctor, and most recent date of medication analysis. A list of the medications currently prescribed and/or taken by the user may be presented on the display 1300. An estimate monthly cost of all the patient's current medications may be presented in a monthly estimated cost tab 1302. In the example shown in display 1300, the predicted monthly cost of all of the user's medication may be $150.

Further, the cost of each medication may be itemized below the monthly estimated cost tab 1302. Thus, next to each medication, an estimated cost for that medication may be presented in a cost tab 1304. In some examples, the cost may be a one-time cost for the medication or a cost per treatment. In another example, the cost may be a period or interval cost, such as a monthly cost for the medication. In yet further examples, the cost may be a yearly cost. It should be appreciated, the cost may be the cost of the medication at a time interval more or less than a year. The costs may be normalized for comparison purposes. Further, the general purpose and intended use of each medication may also be provided under the name of each medication, so that the user may easily keep track of their medications, and for what condition they are taking each medication.

Additionally, each medication may be color coded to indicate the risk of that medication. In one example, if a medication is high risk, a list of alternative medication used to treat the same condition, but having a lower risk, may be provided next to the current medication. In the example shown display 1300 Ambien may be a high risk medication for treating insomnia because it is highly addictive, however alternative medications that also treat insomnia but are not as addictive as Ambien may be presented to the user such as Lunesta, and Melatonin.

In another embodiment, display 1300 may be presented to a user as part of an intervention program as described above with reference to FIG. 1. Display 1300 may be sent as a message, alert, and/or notification to a user via wireless communication such as email, text message, instant message, etc. Thus, if a user selects a medication that may present more than a threshold amount of health risk to the user, display 1300 may automatically be generated and subsequently sent to the user. The health risk may be identified based on information provided by the user and stored in the user profile. Further, the health risk may be presented to the user in a health risk block 1308, next to the medication that poses the health risk. For example, one of the medications may pose a serious health risk when taken in combination with another one of the user's current medications. Said another way, the interaction of two or more medications when taken together may pose a serious health risk to a user. Thus, the user may receive a notification if one, or a combination of two or more of their current medications pose a serious health risk to the user. In the example shown in FIG. 8F, Ambien is identified as being a health risk to the user. The medication may be a health risk because of its addictiveness. Although Ambien may be used to treat insomnia, other less addictive medications, are available to treat insomnia as well. As such, the display 1300 may include showing the user alternative medications used for the same purpose as current high risk medications.

Additionally, the user's care provider may be notified of the health risk posed to the user. The user may receive information as to why they received the intervention notification, as well as information regarding options available for the user. For example, the display 1300 may include giving the user the option to call their care provider, or get a second opinion.

In another embodiment, the intervention program presented in display 1300 may be triggered by the user's care provider which may be their medical doctor. For example, a user's care provider may also have access to the user's medication profile, and may identify potential health risks associated with one or more of the user's medications.

Turning now to FIG. 8G, it shows an example display 1400 that may be presented to a user as part of the intervention program described above with reference to FIG. 8F. However, in the example shown in FIG. 8G, the display 1400 may be presented to a user, after a user has been taking a medication for a threshold duration. The threshold duration may be a duration of medication use such as a number of prescription re-fills, and/or it may be an amount of time such as one month. In the example shown in FIG. 8G, the display 1400 may be presented to a user after the using has been taking testosterone therapy for a threshold duration. Thus, display 1400, may be presented to a user after the using has been taking a medication that may pose a moderate health risk to the user and/or may be more expensive than other medication alternatives. In another example, display 1400 may additionally or alternatively be presented to a user if a medication has less than a threshold grade. In the example shown in display 1400, the testosterone therapy has a grade of "D," which may be lower than the threshold grade.

Thus, display 1400 may present simultaneously, and side-by-side, the current medication of the user, and other alternative medications that have a higher personalized grade than the current medication. Further, information about the clinical effectiveness of the medications may additionally be presented. Specific studies may even be referenced in display 1400 to provide evidence for the effectiveness of the alternative medications. Additionally, the cost of the current medication and the alternative medications may also be provided. Thus, the display 1400 may include a user's current medication, and alternative medications, the personalized grade for each medication, which may be a letter grade, clinical effectiveness of the medications, and cost.

As such, the intervention program may also include notifying a user when a medication may not be effective, and may result in the user paying more money for a medication that may not be as effective as less expensive alternatives. Therefore, display 1400 also shows a user, alternative medication and/or treatment options that are more effective than their current medication, and may be less expensive. In the example shown in FIG. 8G, exercise and weight loss have a higher grade than testosterone therapy. Thus, the predicted effectiveness of exercise and weight loss may be greater than testosterone therapy in improving mood, energy, libido, etc.

Display 1400 may further include presenting questions to a user, for a user to judge their experience with the medication. Thus, the questions may ask the user how effective the medication and/or therapy has been in treating the medical condition of the user. The display 1400 may further prompt the user to contact their care provider to discuss alternative medication options.

Thus, display 1300 shown in FIG. 8F, may be presented to a user immediately or shortly after a user selects a medication that poses an immediate and/or serious health risk to the user. As such, display 1300 may be presented as an alert to the user, to increase prevention of potential health risks to a user. Display 1400, shown in FIG. 8G, may be presented to a user after a duration of medication use, to help a user find more effective treatments at a reduced cost. Said another way, display 1400 may increase the transparency of medication options to a user, and may help a user select a more effective and less-costly medication option than their current medication.

While the above description relates to systems and methods for grading medications, specifically prescription medications, it should be appreciated that in other embodiments the above systems and methods may be applied in a similar manner as described above with other forms of care treatment with or without the example of medications or prescriptions. Said another way, the example control and estimation routines described herein can be used with various forms of care treatment. Other forms of care treatment may include, alone or in combination with one more of the other care treatments: lifestyle choices, exercise, dieting, medical procedures, alternative therapies such as acupuncture, chiropractic care, homeopathy, massage therapy, naturopathy, etc. In this way, systems and methods for a healthcare platform may include grading care treatment options, and presenting said treatment options simultaneously to a user on a user device. Thus, a user may be able to compare medication options, alternative therapies, and other treatment options based on their effectiveness, cost, user experience reviews, care provider recommendations, side effects, and health risks.

As such, a healthcare platform and user interface is provided that may allow a user to search for medications by medication or condition. If the user searches by condition, a plurality of medications used to treat the condition may be presented to the user side by side. Each medication option may have medication information regarding its price, user personalized grade, prescription experience data, user reviews, care provider recommendations, secondary technical effects including side effects, health risks, safety, etc. Further, a user may sort medication options by cost, and/or user personalized grade of the medication. The user personalized grade of the medication may be determined by examining peer reviewed literature, clinical studies, scientific literature, etc., in which the medication was studied. The results of those studies may be evaluated, and the user personalized grade assigned to each medication may be based on one or more of the: confidence of the study results, reliability of the study results, and the effectiveness of the medication in treating the condition and/or alleviating its symptoms. Further, the effectiveness of the medication may be determined based on a weighted score of the participants in the one or more studies pertaining to the medication. Specifically, the results from patients in the studies with more shared characteristics to the user may be weighted more heavily than patients sharing fewer characteristics to the user. As such, the accuracy of the predicted effectiveness of a medication for a user may be improved and be user-specific. Said another way, the predicted effectiveness of a medication in treating a condition of a user, may be specifically tailored and personalized for that user, based on personal information of the user, a medical history of the user, current medication taken by the user, etc.

In addition to comparing medications based on their predicted effectiveness, cost, side effects, user reviews, doctor recommendation, etc., a user may also purchase the medications through the healthcare platform. Further, a user may create a user profile which may contain personal information about the user, a medical history of the user, current medication prescribed and/or taken by the user. The user's doctor and/or care provider may have access to the user profile. As such, a care provider may intervene and prevent a user from purchasing a particular medication if there is a significant enough health risk involved. Additionally and/or alternatively, the user may automatically be notified of potential health risks associated with one or more of the medications they are currently taking. Thus, the healthcare platform may streamline all aspects of health care service for a user onto one user device. A user, may search, compare, select, purchase, provide feedback, and receive warnings after purchase, regarding medications, prescriptions medications, medications, treatment plans, etc.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A method, comprising:

providing, for a user, remote access to a server over a network via a remote user device communicably coupled to the network, wherein the server includes a logic subsystem;

providing, for one or more health care providers, remote access to the server over the network via one or more remote servers communicably coupled to the network;

responsive to a query from the user via the remote user device, the server executing machine readable instructions stored on the logic subsystem for:

querying a first database of a non-transitory remote storage device communicably coupled to the network for user information including one or more characteristics of the user;

querying a second database of the non-transitory remote storage device for a list of medications and medication information about each medication in the list of medications, based on the query from the user;

retrieving the queried user information from the first database;

retrieving the queried list of medications and the medication information for each medication in the list of medications from the second database, wherein the medication information includes an indication of a clinical effectiveness of each medication, prescription experience data characterizing experiences of patients with each medication in the list of medications, cost factor, insurance coverage, and technical secondary effects;

correlating the user information retrieved from the first database with the medication information retrieved from the second database;

calculating a user personalized grade for each medication in the list of medications based on the correlated medication information and user information;

transmitting the user personalized grade and the medication information to the remote user device over the network;

transmitting the user information and the medication information to the one or more health care providers on the one or more remote servers over the network;

receiving one or more health risk notifications from the one or more health care providers via the one or more remote servers;

displaying to the user, on a display of the remote user device, a compare selection that presents a compare display screen, the compare display screen displaying a first selection of a subset of medications from the list of medications, and further displaying display information including displaying the cost factor simultaneously with each of the user personalized grade, the prescription experience data, and the technical secondary effects for each identified medication in the list of medications, where the display information for each identified medication is directly adjacent to the display information for at least one other identified medication, where the display information for at least one identified medication is horizontally aligned with the display information for at least one other identified medication, and where the user personalized grade is displayed in a larger font size than a font size of other displayed text; and thereafter receiving the first selection from the user via the remote user device of the selected subset for comparison;

displaying to the user, on the display, the compare display screen;

receiving a second selection from the user via the remote user device of a medication from the selected subset as a selected medication;

receiving a purchase request from the user via the remote user device for the selected medication;

determining whether the selected medication poses more than a threshold amount of risk to the user based on one of the received health risk notifications; and responsive to the selected medication posing more than the threshold amount of risk to the user:

immediately displaying to the user, on the display of the remote user device, an intervention program based on the one of the received health risk notifications; and preventing the user from purchasing the selected medication posing more than the threshold amount of risk to the user by not fulfilling the purchase request.

2. The method of claim 1, wherein the server further executes machine readable instructions stored on the logic subsystem for alerting the user, via the remote user device, of an identified medication that poses more than the threshold amount of risk to the user.

3. The method of claim 1, wherein the cost factor is an out-of-pocket cost of each identified medication.

4. The method of claim 1, wherein the prescription experience data includes one or more of comments, reviews, and feedback from patients with experience with each identified medication.

5. The method of claim 1, wherein the technical secondary effects include side effects of each identified medication, which is determined based on evidence from scientific literature.

6. The method of claim 1, wherein the calculated user personalized grade for each of the identified medications is a letter grade.

7. The method of claim 1, wherein the displaying the display information further comprises displaying, for each identified medication, one or more of doctor recommendations, links to scientific studies used in calculating the user personalized grade, and comments from patients.

8. The method of claim 1, wherein the receiving the user information includes receiving both medical and non-medical information.

9. The method of claim 1, wherein the calculating the user personalized grade is based on one or more of the indication of the clinical effectiveness of the medications, the prescription experience data, the cost factor, the insurance coverage, and the technical secondary effects.

10. The method of claim 9, wherein one or more of the indication of the clinical effectiveness of the medications, the prescription experience data, the cost factor, the insurance coverage, and the technical secondary effects are differentially weighted when calculating the user personalized grade, and wherein the clinical effectiveness is assigned a first weight, the first weight being higher than a second weight assigned to at least one of the prescription experience data, the cost factor, the insurance coverage, and the technical secondary effects.

11. The method of claim 1, wherein the calculating the user personalized grade is based on one or more clinical studies, and wherein the calculating is further based on an amount of similarity between the user and patients in the one or more clinical studies, where results from clinical studies having greater similarity between the user and patients of the clinical studies are assigned a first weight, the first weight being higher than a second weight assigned to clinical studies having less similarity between the user and patients of the clinical studies.

12. The method of claim 1, wherein the query comprises a specific medication.

13. The method of claim 1, wherein the query comprises a medical condition.

14. A system for displaying medication options and receiving medication selections, the system comprising:
one or more first remote servers, each of the one or more first remote servers comprising one or more storage devices, the one or more storage devices containing information about health care claims and medications;
one or more second remote servers, each of the one or more second remote servers configured for one or more health care providers;
a remote device configured for a user;
a server comprising a health care platform, the server being in wireless communication with the remote device, the one or more first remote servers, and the one or more second remote servers, the server further comprising a storage device and a logic system, the logic system storing computer readable instructions executable by said server, whereby said server is operative to:
receive user information including one or more characteristics of the user from the remote device;
responsive to a query from the user via the remote device, receive a list of medications identified from the one or more storage devices;
receive medication information about each identified medication in the list of medications from the one or more storage devices, wherein the received medication information includes an indication of a clinical effectiveness of the identified medications, prescription experience data characterizing experiences of patients with the identified medications, cost information, insurance coverage, and technical secondary effects;
calculate a user personalized grade for each of the identified medications based on the medication information and the user information;
transmit the user personalized grade and the medication information to the remote device;
transmit the user information and the medication information to the one or more health care providers on the one or more second remote servers;
receive one or more health risk notifications from the one or more health care providers;
display, on a display of the remote device, a compare selection that generates a compare display screen, the compare display screen displaying a first selection of a subset of medications from the list of medications, and further display first display information including displaying the cost information simultaneously with each of the user personalized grade, the prescription experience data, and the technical secondary effects for each identified medication in the list of medications, where the first display information for each identified medication is arranged in one or more rows and two or more columns of a matrix; and thereafter
receive the first selection from the user via the remote device of the selected subset for comparison;
display, on the display of the remote device, the compare display screen over the matrix, the compare display screen further displaying second display information including each of the first display information and additional medication information for each medication in the selected subset;
receive a second selection from the user via the remote device of a medication from the selected subset as a selected medication;
receive a purchase request from the user via the remote device for the selected medication;
determine whether the selected medication presents a potential health risk to the user based on one of the received health risk notifications; and
responsive to the selected medication presenting the potential health risk to the user:
display, on the display of the remote device, a list of one or more alternative medications, wherein each alternative medication has been determined to present a lower health risk to the user than the selected medication; and
prevent the user from purchasing the selected medication presenting the potential health risk to the user by not fulfilling the purchase request.

15. The system of claim 14, wherein the remote device comprises a user interface for displaying the medication information, and wherein the user interface is one or more of an LCD screen, a touch screen, an LED screen, a plasma screen, and a CRT screen.

16. The method of claim 1, wherein the server further executes machine readable instructions stored on the logic subsystem for displaying simultaneously to the user, on the display of the remote user device, one or more sorted positive review comments from other users for the selected medication, one or more sorted negative review comments from other users for the selected medication, and a rating tab for adding a medication review for the selected medication.

17. The system of claim 14, wherein the second display information for at least one medication in the selected subset is horizontally aligned with the second display information for at least one other medication in the selected subset.

18. A method, comprising:
providing, for a user, remote access to a server over a first network via a user device communicably coupled to the first network, wherein the server includes a logic subsystem, the logic subsystem storing machine readable instructions executable by the server;
retrieving, by the server, user information including one or more characteristics of the user from the user device; and
responsive to a query from the user via the user device, the server being operative to:
retrieve a list of a plurality of medications and medication information for each medication in the list of medications from a non-transitory storage device communicably coupled to a second network, where the non-transitory storage device further stores insurance claims data, and wherein the medication information includes an indication of a clinical effectiveness of each medication, prescription experience data characterizing experiences of patients with each medication, a cost factor calculated from the insurance claims data, insurance coverage, and technical secondary effects;
correlate the user information with the medication information;

calculate a user personalized letter grade for each medication in the list of medications based on the correlated user information and medication information;

transmit the user personalized letter grade and the medication information to the user device over the first network;

display to the user, on a display of the user device, a compare selection that provides a compare display screen, the compare display screen displaying a first selection of a subset of medications from the list of medications, and further display display information including displaying the cost factor simultaneously with each of the user personalized letter grade, the cost factor, the prescription experience data, and the technical secondary effects for each medication in the list of medications, where the display information for each medication is displayed as an element of a matrix directly adjacent to another element of the matrix containing the display information for at least one other medication, and where at least two elements of the matrix are horizontally aligned with one another; and thereafter receive, from the user via the user device, the first selection of the selected subset for comparison;

display to the user, on the display of the user device, the compare display screen;

receive, from the user via the user device, a second selection of a medication from the selected subset as a selected medication;

receive, from the user via the user device, a purchase request for the selected medication;

determine whether the selected medication presents more than a threshold amount of risk to the user based on the user information; and responsive to the selected medication presenting more than the threshold amount of risk to the user:
  immediately display to the user, on the display of the user device, an automatically generated alert for the selected medication presenting more than the threshold amount of risk to the user; and
  prevent the user from purchasing the selected medication presenting more than the threshold amount of risk to the user by not fulfilling the purchase request.

19. The method of claim 18, wherein the first network and the second network are a single network.

20. The method of claim 18, wherein the first network and the second network are different networks.

* * * * *